(12) United States Patent
Hall et al.

(10) Patent No.: US 11,123,524 B2
(45) Date of Patent: *Sep. 21, 2021

(54) MEDICAL COMPONENT INSERTION DEVICE INCLUDING A RETRACTABLE NEEDLE

(71) Applicant: C. R. Bard, Inc., Murray Hill, NJ (US)

(72) Inventors: John W. Hall, North Salt Lake, UT (US); Ryan C. Patterson, Farmington, UT (US); Charles L. Farnworth, Riverton, UT (US)

(73) Assignee: C. R. Bard, Inc., Franklin Lakes, NJ (US)

(*) Notice: Subject to any disclaimer, the term of this patent is extended or adjusted under 35 U.S.C. 154(b) by 475 days.

This patent is subject to a terminal disclaimer.

(21) Appl. No.: 15/862,380

(22) Filed: Jan. 4, 2018

(65) Prior Publication Data

US 2018/0126125 A1 May 10, 2018

Related U.S. Application Data

(62) Division of application No. 14/750,658, filed on Jun. 25, 2015, now Pat. No. 9,861,792, which is a division
(Continued)

(51) Int. Cl.
*A61M 25/06* (2006.01)
*A61M 29/00* (2006.01)
*A61M 25/09* (2006.01)

(52) U.S. Cl.
CPC .... *A61M 25/0631* (2013.01); *A61M 25/0606* (2013.01); *A61M 25/09* (2013.01);
(Continued)

(58) Field of Classification Search
CPC .......... A61M 25/0631; A61M 25/0606; A61M 25/09; A61M 2025/0656; A61M 2025/0681; A61M 2025/0687
See application file for complete search history.

(56) References Cited

U.S. PATENT DOCUMENTS

| 2,211,975 A | 8/1940 | Hendrickson |
| 2,259,488 A | 10/1941 | Raiche |

(Continued)

FOREIGN PATENT DOCUMENTS

| AU | 691141 B2 | 5/1998 |
| AU | 710967 B2 | 9/1999 |

(Continued)

OTHER PUBLICATIONS

CN 201580022407.7 filed Nov. 2, 2016 Office Action dated Jan. 31, 2019.
(Continued)

*Primary Examiner* — Nathan R Price
*Assistant Examiner* — Courtney B Fredrickson
(74) *Attorney, Agent, or Firm* — Rutan & Tucker LLP

(57) ABSTRACT

A medical insertion device includes an introducer assembly, a needle, and a housing. The introducer assembly includes a dilator coaxially disposed in a sheath, the dilator removably engaged to the sheath in an insertion configuration. The needle is coaxially disposed in the dilator, the needle having a distal tip and a proximal end coupled to a needle hub. The housing may be removably engaged to the dilator. The needle hub is movably disposed in the housing between a first locked position, in which the distal tip of the needle extends a first length from a distal end of the dilator, a second locked position, in which the distal tip of the needle extends a second length from the distal end of the dilator less than the first length, and a third locked position, in which the distal tip of the needle is within the dilator.

12 Claims, 13 Drawing Sheets

Related U.S. Application Data of application No. 13/405,096, filed on Feb. 24, 2012, now Pat. No. 9,095,683.

(60) Provisional application No. 61/446,817, filed on Feb. 25, 2011.

(52) U.S. Cl.
CPC ..... *A61M 29/00* (2013.01); *A61M 2025/0656* (2013.01); *A61M 2025/0681* (2013.01); *A61M 2025/0687* (2013.01)

(56) References Cited

U.S. PATENT DOCUMENTS

| | | | |
|---|---|---|---|
| 2,330,400 A | 9/1943 | Winder | |
| D138,589 S | 8/1944 | Brandenburg | |
| 3,185,151 A | 5/1965 | Czorny | |
| 3,297,030 A | 1/1967 | Czorny et al. | |
| 3,416,567 A | 12/1968 | von Dardel et al. | |
| 3,469,579 A | 9/1969 | Hubert | |
| 3,500,828 A | 3/1970 | Podhora | |
| 3,552,384 A | 1/1971 | Pierie et al. | |
| 3,572,334 A | 3/1971 | Petterson | |
| 3,585,996 A | 6/1971 | Reynolds et al. | |
| 3,589,361 A | 6/1971 | Loper et al. | |
| 3,592,192 A | 7/1971 | Harautuneian | |
| 3,595,230 A | 7/1971 | Suyeoka et al. | |
| 3,610,240 A | 10/1971 | Harautuneian | |
| 3,682,173 A | 8/1972 | Center | |
| 3,766,916 A | 10/1973 | Moorehead et al. | |
| 3,884,242 A | 5/1975 | Bazell et al. | |
| 3,921,631 A | 11/1975 | Thompson | |
| 3,995,628 A | 12/1976 | Gula et al. | |
| 4,027,668 A | 6/1977 | Dunn | |
| 4,037,600 A | 7/1977 | Poncy et al. | |
| 4,079,738 A | 3/1978 | Dunn et al. | |
| 4,106,506 A | 8/1978 | Koehn et al. | |
| 4,177,809 A | 12/1979 | Moorehead | |
| 4,292,970 A | 10/1981 | Hession, Jr. | |
| 4,317,445 A | 3/1982 | Robinson | |
| 4,345,602 A | 8/1982 | Yoshimura et al. | |
| 4,354,491 A | 10/1982 | Marbry | |
| 4,368,730 A | 1/1983 | Sharrock | |
| 4,387,879 A | 6/1983 | Tauschinski | |
| 4,417,886 A | 11/1983 | Frankhouser et al. | |
| 4,449,693 A | 5/1984 | Gereg | |
| 4,456,017 A | 6/1984 | Miles | |
| 4,464,171 A | 8/1984 | Garwin | |
| 4,509,534 A | 4/1985 | Tassin, Jr. | |
| 4,509,945 A | 4/1985 | Kramann et al. | |
| 4,511,359 A | 4/1985 | Vaillancourt | |
| 4,512,766 A | 4/1985 | Vailancourt | |
| 4,525,157 A | 6/1985 | Vaillancourt | |
| 4,581,019 A | 4/1986 | Curelaru et al. | |
| 4,585,440 A | 4/1986 | Tchervenkov et al. | |
| D287,877 S | 1/1987 | Holewinski et al. | |
| 4,728,322 A | 3/1988 | Walker et al. | |
| 4,738,659 A | 4/1988 | Sleiman | |
| 4,747,831 A | 5/1988 | Kulli | |
| 4,767,407 A | 8/1988 | Foran | |
| 4,772,264 A | 9/1988 | Cragg | |
| 4,772,267 A | 9/1988 | Brown | |
| 4,781,703 A | 11/1988 | Walker et al. | |
| 4,792,531 A | 12/1988 | Kakihana | |
| 4,798,193 A | 1/1989 | Giesy et al. | |
| 4,813,934 A | 3/1989 | Engelson et al. | |
| 4,826,070 A | 5/1989 | Kakihana | |
| 4,828,547 A | 5/1989 | Sahi et al. | |
| 4,834,708 A | 5/1989 | Pillari | |
| 4,834,718 A | 5/1989 | McDonald | |
| 4,840,613 A | 6/1989 | Balbierz | |
| 4,840,622 A | 6/1989 | Hardy | |
| 4,842,591 A | 6/1989 | Luther | |
| 4,846,812 A | 7/1989 | Walker et al. | |
| 4,850,961 A | 7/1989 | Wanderer et al. | |
| 4,860,757 A | 8/1989 | Lynch et al. | |
| 4,869,259 A | 9/1989 | Elkins | |
| D304,079 S | 10/1989 | McFarlane | |
| 4,871,358 A | 10/1989 | Gold | |
| 4,874,377 A | 10/1989 | Newgard et al. | |
| 4,883,461 A | 11/1989 | Sawyer | |
| 4,883,699 A | 11/1989 | Aniuk et al. | |
| 4,894,052 A | 1/1990 | Crawford | |
| 4,895,346 A | 1/1990 | Steigerwald | |
| 4,900,307 A | 2/1990 | Kulli | |
| 4,906,956 A | 3/1990 | Kakihana | |
| 4,908,021 A | 3/1990 | McFarlane | |
| 4,909,793 A | 3/1990 | Vining et al. | |
| 4,911,691 A | 3/1990 | Aniuk et al. | |
| 4,913,704 A | 4/1990 | Kurimoto | |
| 4,917,102 A | 4/1990 | Miller et al. | |
| 4,917,668 A | 4/1990 | Haindl et al. | |
| 4,917,671 A | 4/1990 | Chang | |
| 4,929,235 A | 5/1990 | Merry et al. | |
| 4,935,010 A | 6/1990 | Cox et al. | |
| 4,944,725 A | 7/1990 | McDonald | |
| 4,944,728 A | 7/1990 | Carrell et al. | |
| 4,955,863 A | 9/1990 | Walker et al. | |
| 4,961,729 A | 10/1990 | Vaillancourt | |
| 4,966,586 A | 10/1990 | Vaillancourt | |
| 4,966,589 A | 10/1990 | Kaufman | |
| 4,994,042 A | 2/1991 | Vadher | |
| 4,994,047 A | 2/1991 | Walker et al. | |
| 4,995,866 A | 2/1991 | Amplatz et al. | |
| 5,007,901 A | 4/1991 | Shields | |
| 5,009,642 A | 4/1991 | Sahi | |
| 5,019,048 A | 5/1991 | Margolin | |
| 5,019,049 A | 5/1991 | Haining | |
| D318,733 S | 7/1991 | Wyzgala | |
| 5,034,347 A | 7/1991 | Kakihana | |
| 5,047,013 A | 9/1991 | Rossdeutscher | |
| D321,250 S | 10/1991 | Jepson et al. | |
| 5,053,014 A | 10/1991 | Van Heugten | |
| 5,054,501 A | 10/1991 | Chuttani et al. | |
| 5,061,254 A | 10/1991 | Karakelle et al. | |
| 5,064,416 A | 11/1991 | Newgard et al. | |
| 5,078,694 A | 1/1992 | Wallace | |
| 5,078,696 A | 1/1992 | Nedbaluk | |
| 5,078,702 A | 1/1992 | Pomeranz | |
| 5,084,023 A | 1/1992 | Lemieux | |
| 5,085,645 A | 2/1992 | Purdy et al. | |
| 5,088,984 A | 2/1992 | Fields | |
| 5,093,692 A | 3/1992 | Su et al. | |
| 5,098,392 A | 3/1992 | Fleischhacker et al. | |
| 5,098,395 A | 3/1992 | Fields | |
| 5,098,396 A | 3/1992 | Taylor et al. | |
| 5,098,405 A | 3/1992 | Peterson et al. | |
| 5,108,375 A | 4/1992 | Harrison et al. | |
| 5,108,376 A | 4/1992 | Bonaldo | |
| 5,112,312 A | 5/1992 | Luther | |
| 5,116,323 A | 5/1992 | Kreuzer et al. | |
| 5,120,317 A | 6/1992 | Luther | |
| 5,125,906 A | 6/1992 | Fleck | |
| 5,135,487 A | 8/1992 | Morrill et al. | |
| 5,137,515 A | 8/1992 | Hogan | |
| 5,149,326 A | 9/1992 | Woodgrift et al. | |
| 5,154,703 A | 10/1992 | Bonaldo | |
| 5,156,590 A | 10/1992 | Vilmar | |
| 5,156,596 A | 10/1992 | Balbierz et al. | |
| 5,158,544 A | 10/1992 | Weinstein | |
| 5,167,637 A | 12/1992 | Okada et al. | |
| 5,176,650 A * | 1/1993 | Haining | A61M 25/0631 604/164.08 |
| 5,186,168 A | 2/1993 | Spofford et al. | |
| 5,186,712 A | 2/1993 | Kelso et al. | |
| 5,188,607 A | 2/1993 | Wu | |
| 5,190,528 A | 3/1993 | Fonger et al. | |
| 5,192,301 A | 3/1993 | Kamiya et al. | |
| 5,195,974 A | 3/1993 | Hardy | |
| 5,195,980 A | 3/1993 | Catlin | |
| 5,195,985 A | 3/1993 | Hall | |
| 5,205,830 A | 4/1993 | Dassa et al. | |
| 5,215,527 A | 6/1993 | Beck et al. | |

(56) References Cited

U.S. PATENT DOCUMENTS

| | | |
|---|---|---|
| 5,215,528 A | 6/1993 | Purdy et al. |
| 5,217,435 A | 6/1993 | Kring |
| 5,219,335 A | 6/1993 | Willard et al. |
| 5,221,255 A | 6/1993 | Mahurkar et al. |
| 5,222,944 A | 6/1993 | Harris |
| 5,225,369 A | 7/1993 | Su et al. |
| 5,226,899 A | 7/1993 | Lee et al. |
| D338,955 S | 8/1993 | Gresl et al. |
| 5,234,410 A | 8/1993 | Graham et al. |
| 5,242,411 A | 9/1993 | Yamamoto et al. |
| 5,246,426 A | 9/1993 | Lewis et al. |
| 5,246,430 A | 9/1993 | MacFarlane |
| 5,254,107 A | 10/1993 | Soltesz |
| 5,257,980 A | 11/1993 | Van Antwerp et al. |
| 5,267,982 A | 12/1993 | Sylvanowicz |
| 5,269,771 A | 12/1993 | Thomas et al. |
| D345,419 S | 3/1994 | Horrigan et al. |
| 5,290,310 A | 3/1994 | Makower et al. |
| 5,297,546 A | 3/1994 | Spofford et al. |
| 5,312,359 A | 5/1994 | Wallace |
| 5,312,361 A | 5/1994 | Zadini et al. |
| 5,312,363 A | 5/1994 | Ryan et al. |
| 5,320,608 A | 6/1994 | Gerrone |
| 5,322,517 A | 6/1994 | Sircom et al. |
| 5,330,435 A | 7/1994 | Vaillancourt |
| 5,334,159 A | 8/1994 | Turkel |
| 5,338,311 A | 8/1994 | Mahurkar |
| 5,352,205 A | 10/1994 | Dales et al. |
| 5,358,796 A | 10/1994 | Nakamura et al. |
| 5,366,441 A | 11/1994 | Crawford |
| 5,368,661 A | 11/1994 | Nakamura et al. |
| D353,668 S | 12/1994 | Banks et al. |
| 5,376,082 A | 12/1994 | Phelps |
| 5,376,094 A | 12/1994 | Kline |
| 5,380,290 A | 1/1995 | Makower et al. |
| 5,380,292 A | 1/1995 | Wilson |
| 5,395,341 A | 3/1995 | Slater |
| 5,397,311 A | 3/1995 | Walker et al. |
| 5,405,323 A | 4/1995 | Rogers et al. |
| 5,415,177 A | 5/1995 | Zadini et al. |
| 5,415,645 A | 5/1995 | Friend et al. |
| 5,419,766 A | 5/1995 | Chang et al. |
| 5,419,777 A | 5/1995 | Hofling |
| 5,423,760 A | 6/1995 | Yoon |
| 5,425,718 A | 6/1995 | Tay et al. |
| 5,431,506 A | 7/1995 | Masunaga |
| 5,439,449 A | 8/1995 | Mapes et al. |
| 5,445,625 A | 8/1995 | Voda |
| 5,454,785 A | 10/1995 | Smith |
| 5,454,790 A | 10/1995 | Dubrul |
| 5,456,258 A | 10/1995 | Kondo et al. |
| 5,456,668 A | 10/1995 | Ogle, II |
| 5,458,658 A | 10/1995 | Sircom |
| 5,466,230 A | 11/1995 | Davila |
| 5,480,389 A | 1/1996 | McWha et al. |
| 5,482,395 A | 1/1996 | Gasparini |
| 5,484,419 A | 1/1996 | Fleck |
| 5,487,734 A | 1/1996 | Thorne et al. |
| 5,489,273 A | 2/1996 | Whitney et al. |
| 5,496,281 A | 3/1996 | Krebs |
| 5,501,671 A | 3/1996 | Rosen et al. |
| 5,501,675 A | 3/1996 | Erskine |
| 5,507,300 A | 4/1996 | Mukai et al. |
| 5,512,052 A | 4/1996 | Jesch |
| 5,514,108 A | 5/1996 | Stevens |
| 5,520,655 A | 5/1996 | Davila et al. |
| 5,520,657 A | 5/1996 | Sellers et al. |
| D371,195 S | 6/1996 | Krebs |
| 5,522,807 A | 6/1996 | Luther |
| 5,527,290 A | 6/1996 | Zadini et al. |
| 5,527,291 A | 6/1996 | Zadini et al. |
| 5,531,701 A | 7/1996 | Luther |
| 5,531,713 A | 7/1996 | Mastronardi et al. |
| 5,533,988 A | 7/1996 | Dickerson et al. |
| 5,535,785 A | 7/1996 | Werge et al. |
| 5,542,933 A | 8/1996 | Marks |
| 5,554,136 A | 9/1996 | Luther |
| 5,562,629 A | 10/1996 | Haughton et al. |
| 5,562,630 A | 10/1996 | Nichols |
| 5,562,631 A | 10/1996 | Bogert |
| 5,562,633 A | 10/1996 | Wozencroft |
| 5,562,634 A | 10/1996 | Flumene et al. |
| 5,569,202 A | 10/1996 | Kovalic et al. |
| 5,569,217 A | 10/1996 | Luther |
| 5,571,073 A | 11/1996 | Castillo |
| 5,573,510 A | 11/1996 | Isaacson |
| 5,575,777 A | 11/1996 | Cover et al. |
| 5,591,194 A | 1/1997 | Berthiaume |
| 5,599,291 A | 2/1997 | Balbierz et al. |
| 5,599,327 A | 2/1997 | Sugahara et al. |
| 5,609,583 A | 3/1997 | Hakki et al. |
| 5,613,663 A | 3/1997 | Schmidt et al. |
| 5,613,954 A | 3/1997 | Nelson et al. |
| 5,630,802 A | 5/1997 | Moellmann et al. |
| 5,630,823 A | 5/1997 | Schmitz-Rode et al. |
| 5,634,475 A | 6/1997 | Wolvek |
| 5,634,913 A | 6/1997 | Stinger |
| 5,637,091 A | 6/1997 | Hakky et al. |
| 5,645,076 A | 7/1997 | Yoon |
| 5,651,772 A | 7/1997 | Arnett |
| D383,538 S | 9/1997 | Erskine et al. |
| 5,662,622 A | 9/1997 | Gore et al. |
| 5,674,241 A | 10/1997 | Bley et al. |
| 5,676,658 A | 10/1997 | Erskine |
| 5,683,368 A | 11/1997 | Schmidt |
| 5,683,370 A | 11/1997 | Luther et al. |
| 5,685,855 A | 11/1997 | Erskine |
| 5,685,858 A | 11/1997 | Kawand |
| 5,685,860 A | 11/1997 | Chang et al. |
| 5,688,249 A | 11/1997 | Chang et al. |
| 5,693,025 A | 12/1997 | Stevens |
| 5,695,474 A | 12/1997 | Daugherty |
| 5,697,914 A | 12/1997 | Brimhall |
| 5,700,250 A | 12/1997 | Erskine |
| 5,702,367 A | 12/1997 | Cover et al. |
| 5,702,369 A | 12/1997 | Mercereau |
| 5,704,914 A | 1/1998 | Stocking et al. |
| 5,722,425 A | 3/1998 | Bostrom |
| 5,725,503 A | 3/1998 | Arnett |
| 5,730,150 A | 3/1998 | Peppel et al. |
| 5,730,733 A | 3/1998 | Mortier et al. |
| 5,730,741 A | 3/1998 | Horzewski et al. |
| 5,738,144 A | 4/1998 | Rogers |
| 5,738,660 A | 4/1998 | Luther |
| 5,743,882 A | 4/1998 | Luther |
| 5,743,888 A | 4/1998 | Wilkes et al. |
| 5,749,371 A | 5/1998 | Zadini et al. |
| 5,749,857 A | 5/1998 | Cuppy |
| 5,749,861 A | 5/1998 | Guala et al. |
| 5,750,741 A | 5/1998 | Crocker et al. |
| 5,755,693 A | 5/1998 | Walker et al. |
| 5,755,709 A | 5/1998 | Cuppy |
| 5,762,630 A | 6/1998 | Bley et al. |
| 5,762,636 A | 6/1998 | Rupp et al. |
| 5,765,682 A | 6/1998 | Bley et al. |
| 5,779,679 A | 7/1998 | Shaw |
| 5,779,680 A | 7/1998 | Yoon |
| 5,779,681 A | 7/1998 | Bonn |
| 5,782,807 A | 7/1998 | Falvai et al. |
| D397,434 S | 8/1998 | Pike |
| 5,792,124 A | 8/1998 | Horrigan et al. |
| 5,800,395 A | 9/1998 | Botich et al. |
| 5,807,339 A | 9/1998 | Bostrom et al. |
| 5,807,342 A | 9/1998 | Musgrave et al. |
| 5,807,350 A | 9/1998 | Diaz |
| 5,810,780 A | 9/1998 | Brimhall et al. |
| 5,810,835 A | 9/1998 | Ryan et al. |
| 5,813,411 A | 9/1998 | Van Bladel et al. |
| 5,817,058 A | 10/1998 | Shaw |
| 5,817,069 A | 10/1998 | Arnett |
| 5,824,001 A | 10/1998 | Erskine |
| 5,827,202 A | 10/1998 | Miraki et al. |
| 5,827,221 A | 10/1998 | Phelps |
| 5,827,227 A | 10/1998 | DeLago |

(56) References Cited

U.S. PATENT DOCUMENTS

| | | |
|---|---|---|
| 5,830,190 A | 11/1998 | Howell |
| 5,830,224 A | 11/1998 | Cohn et al. |
| 5,839,470 A | 11/1998 | Hiejima et al. |
| 5,843,002 A | 12/1998 | Pecor et al. |
| 5,843,038 A | 12/1998 | Bailey |
| 5,846,259 A | 12/1998 | Berthiaume |
| 5,851,196 A | 12/1998 | Arnett |
| 5,853,393 A | 12/1998 | Bogert |
| 5,855,615 A | 1/1999 | Bley et al. |
| 5,858,002 A | 1/1999 | Jesch |
| 5,865,806 A | 2/1999 | Howell |
| 5,873,864 A | 2/1999 | Luther et al. |
| 5,879,332 A | 3/1999 | Schwemberger et al. |
| 5,879,337 A | 3/1999 | Kuracina et al. |
| 5,885,217 A | 3/1999 | Gisselberg et al. |
| 5,885,251 A | 3/1999 | Luther |
| 5,891,098 A | 4/1999 | Huang |
| 5,891,105 A | 4/1999 | Mahurkar |
| 5,895,398 A | 4/1999 | Wensel et al. |
| 5,902,274 A | 5/1999 | Yamamoto et al. |
| 5,902,832 A | 5/1999 | Van Bladel et al. |
| 5,911,705 A | 6/1999 | Howell |
| 5,911,710 A | 6/1999 | Barry et al. |
| 5,913,848 A | 6/1999 | Luther et al. |
| 5,916,208 A | 6/1999 | Luther et al. |
| 5,928,199 A | 7/1999 | Nakagami |
| D413,382 S | 8/1999 | Maissami |
| 5,935,110 A | 8/1999 | Brimhall |
| 5,941,854 A | 8/1999 | Bhitiyakul |
| 5,944,690 A | 8/1999 | Falwell et al. |
| 5,947,930 A | 9/1999 | Schwemberger et al. |
| 5,951,520 A | 9/1999 | Burzynski et al. |
| 5,954,698 A | 9/1999 | Pike |
| 5,957,893 A | 9/1999 | Luther et al. |
| 5,964,744 A | 10/1999 | Balbierz et al. |
| 5,967,490 A | 10/1999 | Pike |
| 5,984,895 A | 11/1999 | Padilla et al. |
| 5,984,903 A | 11/1999 | Nadal |
| 5,989,220 A | 11/1999 | Shaw et al. |
| 5,989,271 A | 11/1999 | Bonnette et al. |
| 5,997,507 A | 12/1999 | Dysarz |
| 5,997,510 A | 12/1999 | Schwemberger |
| 6,001,080 A | 12/1999 | Kuracina et al. |
| 6,004,278 A | 12/1999 | Botich et al. |
| 6,004,294 A | 12/1999 | Brimhall et al. |
| 6,004,295 A | 12/1999 | Langer et al. |
| 6,011,988 A | 1/2000 | Lynch et al. |
| 6,019,736 A | 2/2000 | Avellanet et al. |
| 6,022,319 A | 2/2000 | Willard et al. |
| 6,024,727 A | 2/2000 | Thorne et al. |
| 6,024,729 A | 2/2000 | Dehdashtian et al. |
| 6,045,734 A | 4/2000 | Luther et al. |
| 6,056,726 A | 5/2000 | Isaacson |
| 6,059,484 A | 5/2000 | Greive |
| 6,066,100 A | 5/2000 | Willard et al. |
| 6,074,378 A | 6/2000 | Mouri et al. |
| 6,077,244 A | 6/2000 | Botich et al. |
| 6,080,137 A | 6/2000 | Pike |
| 6,083,237 A | 7/2000 | Huitema et al. |
| 6,096,004 A | 8/2000 | Meglan et al. |
| 6,096,005 A | 8/2000 | Botich et al. |
| 6,109,264 A | 8/2000 | Sauer |
| 6,117,108 A | 9/2000 | Woehr et al. |
| 6,120,494 A | 9/2000 | Jonkman |
| 6,126,633 A * | 10/2000 | Kaji .................. A61M 25/0084 604/164.01 |
| 6,126,641 A | 10/2000 | Shields |
| 6,139,532 A | 10/2000 | Howell et al. |
| 6,139,557 A | 10/2000 | Passafaro et al. |
| 6,159,179 A | 12/2000 | Simonson |
| 6,171,234 B1 | 1/2001 | White et al. |
| 6,171,287 B1 | 1/2001 | Lynn et al. |
| 6,176,842 B1 | 1/2001 | Tachibana et al. |
| 6,193,690 B1 | 2/2001 | Dysarz |
| 6,197,001 B1 | 3/2001 | Wilson et al. |
| 6,197,007 B1 | 3/2001 | Thorne et al. |
| 6,197,041 B1 | 3/2001 | Shichman et al. |
| 6,203,527 B1 | 3/2001 | Zadini et al. |
| 6,213,978 B1 | 4/2001 | Voyten |
| 6,217,558 B1 | 4/2001 | Zadini et al. |
| 6,221,047 B1 | 4/2001 | Greene et al. |
| 6,221,048 B1 | 4/2001 | Phelps |
| 6,221,049 B1 | 4/2001 | Selmon et al. |
| 6,224,569 B1 | 5/2001 | Brimhall |
| 6,228,060 B1 | 5/2001 | Howell |
| 6,228,062 B1 | 5/2001 | Howell et al. |
| 6,228,073 B1 | 5/2001 | Noone et al. |
| 6,245,045 B1 | 6/2001 | Stratienko |
| 6,251,092 B1 | 6/2001 | Qin et al. |
| 6,268,399 B1 | 7/2001 | Hultine et al. |
| 6,270,480 B1 | 8/2001 | Dorr et al. |
| 6,273,871 B1 | 8/2001 | Davis et al. |
| 6,280,419 B1 | 8/2001 | Vojtasek |
| 6,287,278 B1 | 9/2001 | Woehr et al. |
| 6,309,379 B1 | 10/2001 | Willard et al. |
| 6,319,244 B2 | 11/2001 | Suresh et al. |
| 6,322,537 B1 | 11/2001 | Chang |
| D452,003 S | 12/2001 | Niermann |
| 6,325,781 B1 | 12/2001 | Takagi et al. |
| 6,325,797 B1 | 12/2001 | Stewart et al. |
| 6,336,914 B1 | 1/2002 | Gillespie, III |
| 6,352,520 B1 | 3/2002 | Miyazaki |
| 6,368,337 B1 | 4/2002 | Kieturakis et al. |
| 6,379,333 B1 | 4/2002 | Brimhall et al. |
| 6,379,372 B1 | 4/2002 | Dehdashtian et al. |
| D457,955 S | 5/2002 | Bilitz |
| 6,406,442 B1 | 6/2002 | McFann et al. |
| D460,179 S | 7/2002 | Isoda et al. |
| 6,422,989 B1 | 7/2002 | Hektner |
| 6,436,070 B1 | 8/2002 | Botich et al. |
| 6,436,112 B2 | 8/2002 | Wensel et al. |
| 6,443,929 B1 | 9/2002 | Kuracina et al. |
| 6,451,052 B1 | 9/2002 | Burmeister et al. |
| 6,461,362 B1 | 10/2002 | Halseth et al. |
| 6,475,217 B1 | 11/2002 | Platt |
| 6,478,779 B1 | 11/2002 | Hu |
| 6,485,473 B1 | 11/2002 | Lynn |
| 6,485,497 B2 | 11/2002 | Wensel et al. |
| 6,497,681 B1 | 12/2002 | Brenner |
| 6,506,181 B2 | 1/2003 | Meng et al. |
| 6,514,236 B1 | 2/2003 | Stratienko |
| 6,524,276 B1 | 2/2003 | Halseth et al. |
| D471,980 S | 3/2003 | Caizza |
| 6,527,759 B1 | 3/2003 | Tachibana et al. |
| 6,530,913 B1 | 3/2003 | Giba et al. |
| 6,530,935 B2 | 3/2003 | Wensel et al. |
| 6,540,725 B1 | 4/2003 | Ponzi |
| 6,540,732 B1 | 4/2003 | Botich et al. |
| 6,544,239 B2 | 4/2003 | Kinsey et al. |
| 6,547,762 B1 | 4/2003 | Botich et al. |
| 6,558,355 B1 | 5/2003 | Metzger et al. |
| 6,582,402 B1 | 6/2003 | Erskine |
| 6,582,440 B1 | 6/2003 | Brumbach |
| 6,585,703 B1 | 7/2003 | Kassel et al. |
| 6,589,262 B1 | 7/2003 | Honebrink et al. |
| 6,595,955 B2 | 7/2003 | Ferguson et al. |
| 6,595,959 B1 | 7/2003 | Stratienko |
| 6,607,511 B2 | 8/2003 | Halseth et al. |
| 6,616,630 B1 | 9/2003 | Woehr et al. |
| 6,620,136 B1 | 9/2003 | Pressly, Sr. et al. |
| 6,623,449 B2 | 9/2003 | Paskar |
| 6,623,456 B1 | 9/2003 | Holdaway et al. |
| 6,626,868 B1 | 9/2003 | Prestidge et al. |
| 6,626,869 B1 | 9/2003 | Bint |
| 6,629,959 B2 | 10/2003 | Kuracina et al. |
| 6,632,201 B1 | 10/2003 | Mathias et al. |
| 6,638,252 B2 | 10/2003 | Moulton et al. |
| 6,641,564 B1 | 11/2003 | Kraus |
| 6,645,178 B1 | 11/2003 | Junker et al. |
| 6,652,486 B2 | 11/2003 | Bialecki et al. |
| 6,652,490 B2 | 11/2003 | Howell |
| 6,663,577 B2 | 12/2003 | Jen et al. |
| 6,663,592 B2 | 12/2003 | Rhad et al. |
| 6,666,865 B2 | 12/2003 | Platt |

(56) References Cited

U.S. PATENT DOCUMENTS

| | | |
|---|---|---|
| 6,679,900 B2 | 1/2004 | Kieturakis et al. |
| 6,689,102 B2 | 2/2004 | Greene |
| 6,692,508 B2 | 2/2004 | Wensel et al. |
| 6,692,509 B2 | 2/2004 | Wensel et al. |
| 6,695,814 B2 | 2/2004 | Greene et al. |
| 6,695,856 B2 | 2/2004 | Kieturakis et al. |
| 6,695,860 B1 | 2/2004 | Ward et al. |
| 6,699,221 B2 | 3/2004 | Vaillancourt |
| 6,702,811 B2 | 3/2004 | Stewart et al. |
| 6,706,018 B2 | 3/2004 | Westlund et al. |
| 6,711,444 B2 | 3/2004 | Koblish |
| 6,712,790 B1 | 3/2004 | Prestidge et al. |
| 6,712,797 B1 | 3/2004 | Southern, Jr. |
| 6,716,197 B2 | 4/2004 | Svendsen |
| 6,730,062 B2 | 5/2004 | Hoffman et al. |
| 6,740,063 B2 | 5/2004 | Lynn |
| 6,740,096 B2 | 5/2004 | Teague et al. |
| 6,745,080 B2 | 6/2004 | Koblish |
| 6,749,588 B1 | 6/2004 | Howell et al. |
| 6,764,468 B1 | 7/2004 | East |
| D494,270 S | 8/2004 | Reschke |
| 6,776,788 B1 | 8/2004 | Klint et al. |
| 6,796,962 B2 | 9/2004 | Ferguson et al. |
| 6,824,545 B2 | 11/2004 | Sepetka et al. |
| 6,832,715 B2 | 12/2004 | Eungard et al. |
| 6,835,190 B2 | 12/2004 | Nguyen |
| 6,837,867 B2 | 1/2005 | Kortelling |
| 6,860,871 B2 | 3/2005 | Kuracina et al. |
| 6,872,193 B2 | 3/2005 | Shaw et al. |
| 6,887,220 B2 | 5/2005 | Hogendijk |
| 6,902,546 B2 | 6/2005 | Ferguson |
| 6,905,483 B2 | 6/2005 | Newby et al. |
| 6,913,595 B2 | 7/2005 | Mastorakis |
| 6,916,311 B2 | 7/2005 | Vojtasek |
| 6,921,386 B2 | 7/2005 | Shue et al. |
| 6,921,391 B1 | 7/2005 | Barker et al. |
| 6,929,624 B1 | 8/2005 | Del Castillo |
| 6,939,325 B2 | 9/2005 | Haining |
| 6,942,652 B1 | 9/2005 | Pressly, Sr. et al. |
| 6,953,448 B2 | 10/2005 | Moulton et al. |
| 6,958,054 B2 | 10/2005 | Fitzgerald |
| 6,958,055 B2 | 10/2005 | Donnan et al. |
| 6,960,191 B2 | 11/2005 | Howlett et al. |
| 6,972,002 B2 | 12/2005 | Thorne |
| 6,974,438 B2 | 12/2005 | Shekalim |
| 6,994,693 B2 | 2/2006 | Tal |
| 7,001,396 B2 | 2/2006 | Glazier et al. |
| 7,004,927 B2 | 2/2006 | Ferguson et al. |
| 7,008,404 B2 | 3/2006 | Nakajima |
| 7,018,372 B2 | 3/2006 | Casey et al. |
| 7,018,390 B2 | 3/2006 | Turovskiy et al. |
| 7,025,746 B2 | 4/2006 | Tal |
| 7,029,467 B2 | 4/2006 | Currier et al. |
| 7,033,335 B2 | 4/2006 | Haarala et al. |
| 7,044,935 B2 | 5/2006 | Shue et al. |
| 7,060,055 B2 | 6/2006 | Wilkinson et al. |
| 7,090,656 B1 | 8/2006 | Botich et al. |
| 7,094,243 B2 | 8/2006 | Mulholland et al. |
| 7,097,633 B2 | 8/2006 | Botich et al. |
| 7,125,396 B2 | 10/2006 | Leinsing et al. |
| 7,125,397 B2 | 10/2006 | Woehr et al. |
| 7,141,040 B2 | 11/2006 | Lichtenberg |
| 7,153,276 B2 | 12/2006 | Barker et al. |
| 7,163,520 B2 | 1/2007 | Bernard et al. |
| 7,169,159 B2 | 1/2007 | Green et al. |
| 7,179,244 B2 | 2/2007 | Smith et al. |
| 7,186,239 B2 | 3/2007 | Woehr |
| 7,191,900 B2 | 3/2007 | Opie et al. |
| 7,192,433 B2 | 3/2007 | Osypka et al. |
| 7,204,813 B2 | 4/2007 | Shue et al. |
| 7,214,211 B2 | 5/2007 | Woehr et al. |
| 7,264,613 B2 | 9/2007 | Woehr et al. |
| 7,291,130 B2 | 11/2007 | McGurk |
| 7,303,547 B2 | 12/2007 | Pressly, Sr. et al. |
| 7,303,548 B2 | 12/2007 | Rhad et al. |
| 7,314,462 B2 | 1/2008 | O'Reagan et al. |
| 7,331,966 B2 | 2/2008 | Soma et al. |
| 7,344,516 B2 | 3/2008 | Erskine |
| 7,354,422 B2 | 4/2008 | Riesenberger et al. |
| 7,374,554 B2 | 5/2008 | Menzi et al. |
| 7,381,205 B2 | 6/2008 | Thommen |
| 7,396,346 B2 | 7/2008 | Nakajima |
| 7,413,562 B2 | 8/2008 | Ferguson et al. |
| 7,422,572 B2 | 9/2008 | Popov et al. |
| 7,458,954 B2 | 12/2008 | Ferguson et al. |
| 7,465,294 B1 | 12/2008 | Vladimirsky |
| 7,468,057 B2 | 12/2008 | Ponzi |
| 7,470,254 B2 | 12/2008 | Basta et al. |
| 7,491,176 B2 | 2/2009 | Mann |
| 7,494,010 B2 | 2/2009 | Opie et al. |
| 7,500,965 B2 | 3/2009 | Menzi et al. |
| 7,507,222 B2 | 3/2009 | Cindrich et al. |
| 7,513,887 B2 | 4/2009 | Halseth et al. |
| 7,513,888 B2 | 4/2009 | Sircom et al. |
| 7,524,306 B2 | 4/2009 | Botich et al. |
| 7,530,965 B2 | 5/2009 | Villa et al. |
| 7,534,227 B2 | 5/2009 | Kulli |
| 7,534,231 B2 | 5/2009 | Kuracina et al. |
| 7,544,170 B2 | 6/2009 | Williams et al. |
| 7,556,617 B2 | 7/2009 | Voorhees, Jr. et al. |
| 7,566,323 B2 | 7/2009 | Chang |
| D601,243 S | 9/2009 | Bierman et al. |
| 7,597,681 B2 | 10/2009 | Sutton et al. |
| 7,608,057 B2 | 10/2009 | Woehr et al. |
| D604,839 S | 11/2009 | Crawford et al. |
| 7,611,485 B2 | 11/2009 | Ferguson |
| 7,611,487 B2 | 11/2009 | Woehr et al. |
| 7,611,499 B2 | 11/2009 | Woehr et al. |
| 7,618,395 B2 | 11/2009 | Ferguson |
| 7,625,360 B2 | 12/2009 | Woehr et al. |
| 7,628,769 B2 | 12/2009 | Grandt et al. |
| 7,632,243 B2 | 12/2009 | Bialecki et al. |
| 7,645,263 B2 | 1/2010 | Angel et al. |
| 7,654,988 B2 | 2/2010 | Moulton et al. |
| 7,658,725 B2 | 2/2010 | Bialecki et al. |
| D612,043 S | 3/2010 | Young et al. |
| 7,678,080 B2 | 3/2010 | Shue et al. |
| 7,682,358 B2 | 3/2010 | Gullickson et al. |
| 7,691,088 B2 | 4/2010 | Howell |
| 7,691,090 B2 | 4/2010 | Belley et al. |
| 7,691,093 B2 | 4/2010 | Brimhall |
| 7,695,458 B2 | 4/2010 | Belley et al. |
| 7,699,807 B2 | 4/2010 | Faust et al. |
| D615,197 S | 5/2010 | Koh et al. |
| 7,708,721 B2 | 5/2010 | Khaw |
| 7,713,243 B2 | 5/2010 | Hillman |
| 7,717,875 B2 | 5/2010 | Knudson et al. |
| 7,722,567 B2 | 5/2010 | Tal |
| 7,722,569 B2 | 5/2010 | Soderholm et al. |
| D617,893 S | 6/2010 | Bierman et al. |
| 7,731,687 B2 | 6/2010 | Menzi et al. |
| 7,731,691 B2 | 6/2010 | Cote et al. |
| 7,736,332 B2 | 6/2010 | Carlyon et al. |
| 7,736,337 B2 | 6/2010 | Diep et al. |
| 7,736,339 B2 | 6/2010 | Woehr et al. |
| 7,736,342 B2 | 6/2010 | Abriles et al. |
| 7,740,615 B2 | 6/2010 | Shaw et al. |
| 7,744,574 B2 | 6/2010 | Pederson et al. |
| 7,753,877 B2 | 7/2010 | Bialecki et al. |
| 7,753,887 B2 | 7/2010 | Botich et al. |
| 7,762,984 B2 | 7/2010 | Kumoyama et al. |
| 7,762,993 B2 | 7/2010 | Perez |
| 7,766,879 B2 | 8/2010 | Tan et al. |
| 7,776,052 B2 | 8/2010 | Greenberg et al. |
| 7,785,296 B2 | 8/2010 | Muskatello et al. |
| 7,794,424 B2 | 9/2010 | Paskar |
| 7,798,994 B2 | 9/2010 | Brimhall |
| 7,803,142 B2 | 9/2010 | Longson et al. |
| 7,828,773 B2 | 11/2010 | Swisher et al. |
| 7,828,774 B2 | 11/2010 | Harding et al. |
| 7,833,201 B2 | 11/2010 | Carlyon et al. |
| 7,850,644 B2 | 12/2010 | Gonzalez et al. |
| 7,857,770 B2 | 12/2010 | Raulerson et al. |
| D634,843 S | 3/2011 | Kim et al. |

(56) References Cited

U.S. PATENT DOCUMENTS

| | | |
|---|---|---|
| 7,896,862 B2 | 3/2011 | Long et al. |
| 7,905,857 B2 | 3/2011 | Swisher |
| 7,914,488 B2 | 3/2011 | Dickerson |
| 7,914,492 B2 | 3/2011 | Heuser |
| 7,922,696 B2 | 4/2011 | Tal et al. |
| 7,922,698 B2 | 4/2011 | Riesenberger et al. |
| 7,927,314 B2 | 4/2011 | Kuracina et al. |
| 7,935,080 B2 | 5/2011 | Howell et al. |
| 7,959,613 B2 | 6/2011 | Rhad et al. |
| 7,972,313 B2 | 7/2011 | Woehr et al. |
| 7,972,324 B2 | 7/2011 | Quint |
| D643,531 S | 8/2011 | van der Weiden |
| 8,029,470 B2 | 10/2011 | Whiting et al. |
| 8,029,472 B2 | 10/2011 | Leinsing et al. |
| 8,048,031 B2 | 11/2011 | Shaw et al. |
| 8,048,039 B2 | 11/2011 | Carlyon et al. |
| 8,057,404 B2 | 11/2011 | Fujiwara et al. |
| 8,062,261 B2 | 11/2011 | Adams |
| 8,075,529 B2 | 12/2011 | Nakajima et al. |
| 8,079,979 B2 | 12/2011 | Moorehead |
| D653,329 S | 1/2012 | Lee-Sepsick |
| 8,100,858 B2 | 1/2012 | Woehr et al. |
| 8,105,286 B2 | 1/2012 | Anderson et al. |
| 8,105,315 B2 | 1/2012 | Johnson et al. |
| 8,123,727 B2 | 2/2012 | Luther et al. |
| 8,152,758 B2 | 4/2012 | Chan et al. |
| 8,162,881 B2 | 4/2012 | Lilley, Jr. et al. |
| 8,167,851 B2 | 5/2012 | Sen |
| 8,177,753 B2 | 5/2012 | Vitullo et al. |
| RE43,473 E | 6/2012 | Newby et al. |
| 8,192,402 B2 | 6/2012 | Anderson et al. |
| 8,202,251 B2 | 6/2012 | Bierman et al. |
| 8,202,253 B1 | 6/2012 | Wexler |
| 8,206,343 B2 | 6/2012 | Racz |
| 8,211,070 B2 | 7/2012 | Woehr et al. |
| 8,221,387 B2 | 7/2012 | Shelso et al. |
| 8,226,612 B2 | 7/2012 | Nakajima |
| 8,235,945 B2 | 8/2012 | Baid |
| 8,251,923 B2 | 8/2012 | Carrez et al. |
| 8,251,950 B2 | 8/2012 | Albert et al. |
| D667,111 S | 9/2012 | Robinson |
| 8,257,322 B2 | 9/2012 | Koehler et al. |
| 8,273,054 B2 | 9/2012 | St. Germain et al. |
| 8,286,657 B2 | 10/2012 | Belley et al. |
| 8,298,186 B2 | 10/2012 | Popov |
| 8,303,543 B2 | 11/2012 | Abulhaj |
| 8,308,685 B2 | 11/2012 | Botich et al. |
| 8,308,691 B2 | 11/2012 | Woehr et al. |
| D672,456 S | 12/2012 | Lee-Sepsick |
| 8,323,249 B2 | 12/2012 | White et al. |
| 8,328,762 B2 | 12/2012 | Woehr et al. |
| 8,328,837 B2 | 12/2012 | Binmoeller |
| 8,333,735 B2 | 12/2012 | Woehr et al. |
| 8,337,424 B2 | 12/2012 | Palmer et al. |
| 8,337,463 B2 | 12/2012 | Woehr et al. |
| 8,337,471 B2 | 12/2012 | Baid |
| D675,318 S | 1/2013 | Luk et al. |
| 8,361,020 B2 | 1/2013 | Stout |
| 8,361,038 B2 | 1/2013 | McKinnon et al. |
| 8,376,994 B2 | 2/2013 | Woehr et al. |
| 8,377,006 B2 | 2/2013 | Tal et al. |
| 8,382,721 B2 | 2/2013 | Woehr et al. |
| 8,388,583 B2 | 3/2013 | Stout et al. |
| 8,403,886 B2 | 3/2013 | Bialecki et al. |
| 8,412,300 B2 | 4/2013 | Sonderegger |
| 8,414,539 B1 | 4/2013 | Kuracina et al. |
| 8,419,688 B2 | 4/2013 | Woehr et al. |
| 8,444,605 B2 | 5/2013 | Kuracina et al. |
| 8,454,536 B2 | 6/2013 | Raulerson et al. |
| 8,460,247 B2 | 6/2013 | Woehr et al. |
| 8,469,928 B2 | 6/2013 | Stout et al. |
| 8,496,628 B2 | 7/2013 | Erskine |
| D687,548 S | 8/2013 | Hayashi |
| 8,506,533 B2 | 8/2013 | Carlyon et al. |
| 8,509,340 B2 | 8/2013 | Michelitsch |
| 8,517,959 B2 | 8/2013 | Kurosawa et al. |
| 8,529,515 B2 | 9/2013 | Woehr et al. |
| 8,535,271 B2 | 9/2013 | Fuchs et al. |
| 8,540,728 B2 | 9/2013 | Woehr et al. |
| 8,545,454 B2 | 10/2013 | Kuracina et al. |
| 8,568,372 B2 | 10/2013 | Woehr et al. |
| 8,574,203 B2 | 11/2013 | Stout et al. |
| 8,579,881 B2 | 11/2013 | Agro et al. |
| 8,585,651 B2 | 11/2013 | Asai |
| 8,585,660 B2 | 11/2013 | Murphy |
| 8,591,467 B2 | 11/2013 | Walker et al. |
| 8,591,468 B2 | 11/2013 | Woehr et al. |
| 8,597,249 B2 | 12/2013 | Woehr et al. |
| 8,622,931 B2 | 1/2014 | Teague et al. |
| 8,622,972 B2 | 1/2014 | Nystrom et al. |
| D700,318 S | 2/2014 | Amoah et al. |
| 8,647,301 B2 | 2/2014 | Bialecki et al. |
| 8,647,313 B2 | 2/2014 | Woehr et al. |
| 8,647,324 B2 | 2/2014 | DeLegge et al. |
| 8,652,104 B2 | 2/2014 | Goral et al. |
| 8,657,790 B2 | 2/2014 | Tal et al. |
| 8,672,888 B2 | 3/2014 | Tal |
| 8,679,063 B2 | 3/2014 | Stout et al. |
| 8,690,833 B2 | 4/2014 | Belson |
| 8,715,242 B2 | 5/2014 | Helm, Jr. |
| 8,721,546 B2 | 5/2014 | Belson |
| 8,728,030 B2 | 5/2014 | Woehr |
| 8,728,035 B2 | 5/2014 | Warring et al. |
| 8,740,859 B2 | 6/2014 | McKinnon et al. |
| 8,740,964 B2 | 6/2014 | Hartley |
| 8,747,387 B2 | 6/2014 | Belley et al. |
| 8,753,317 B2 | 6/2014 | Osborne et al. |
| 8,764,711 B2 | 7/2014 | Kuracina et al. |
| D710,495 S | 8/2014 | Wu et al. |
| 8,814,833 B2 | 8/2014 | Farrell et al. |
| D713,957 S | 9/2014 | Woehr et al. |
| D714,436 S | 9/2014 | Lee-Sepsick |
| 8,827,965 B2 | 9/2014 | Woehr et al. |
| 8,845,584 B2 | 9/2014 | Ferguson et al. |
| D715,931 S | 10/2014 | Watanabe et al. |
| 8,864,714 B2 | 10/2014 | Harding et al. |
| 8,900,192 B2 | 12/2014 | Anderson et al. |
| 8,932,257 B2 | 1/2015 | Woehr |
| 8,932,258 B2 | 1/2015 | Blanchard et al. |
| 8,932,259 B2 | 1/2015 | Stout et al. |
| 8,945,011 B2 | 2/2015 | Sheldon et al. |
| 8,951,230 B2 | 2/2015 | Tanabe et al. |
| 8,956,327 B2 | 2/2015 | Bierman et al. |
| 8,974,426 B2 | 3/2015 | Corcoran et al. |
| 8,979,802 B2 | 3/2015 | Woehr |
| 8,986,227 B2 | 3/2015 | Belson |
| D726,908 S | 4/2015 | Yu et al. |
| 8,998,852 B2 | 4/2015 | Blanchard et al. |
| 9,005,169 B2 | 4/2015 | Gravesen et al. |
| 9,011,351 B2 | 4/2015 | Hoshinouchi |
| 9,011,381 B2 | 4/2015 | Yamada et al. |
| D728,781 S | 5/2015 | Pierson et al. |
| 9,022,979 B2 | 5/2015 | Woehr |
| 9,033,927 B2 | 5/2015 | Maan et al. |
| D733,289 S | 6/2015 | Blanchard et al. |
| 9,044,583 B2 | 6/2015 | Vaillancourt |
| D735,321 S | 7/2015 | Blanchard |
| 9,089,671 B2 | 7/2015 | Stout et al. |
| 9,089,674 B2 | 7/2015 | Ginn et al. |
| 9,095,683 B2 | 8/2015 | Hall et al. |
| 9,101,746 B2 | 8/2015 | Stout et al. |
| 9,108,021 B2 | 8/2015 | Hyer et al. |
| 9,114,231 B2 | 8/2015 | Woehr et al. |
| 9,114,241 B2 | 8/2015 | Stout et al. |
| 9,126,012 B2 | 9/2015 | McKinnon et al. |
| 9,138,252 B2 | 9/2015 | Bierman et al. |
| 9,138,545 B2 | 9/2015 | Shaw et al. |
| 9,138,559 B2 | 9/2015 | Odland et al. |
| RE45,776 E | 10/2015 | Root et al. |
| D740,410 S | 10/2015 | Korkuch et al. |
| 9,149,625 B2 | 10/2015 | Woehr et al. |
| 9,149,626 B2 | 10/2015 | Woehr et al. |
| 9,155,863 B2 | 10/2015 | Isaacson et al. |
| 9,162,036 B2 | 10/2015 | Caples et al. |

(56) References Cited

U.S. PATENT DOCUMENTS

| | | |
|---|---|---|
| 9,162,037 B2 | 10/2015 | Belson et al. |
| 9,180,275 B2 | 11/2015 | Helm |
| D746,445 S | 12/2015 | Lazarus |
| 9,205,231 B2 | 12/2015 | Call et al. |
| 9,216,109 B2 | 12/2015 | Badawi et al. |
| 9,220,531 B2 | 12/2015 | Datta et al. |
| 9,220,871 B2 | 12/2015 | Thorne et al. |
| 9,220,882 B2 | 12/2015 | Belley et al. |
| D748,254 S | 1/2016 | Freigang et al. |
| 9,227,038 B2 | 1/2016 | Woehr |
| 9,242,071 B2 | 1/2016 | Morgan et al. |
| 9,242,072 B2 | 1/2016 | Morgan et al. |
| RE45,896 E | 2/2016 | Stout et al. |
| D748,774 S | 2/2016 | Caron |
| D748,777 S | 2/2016 | Uenishi et al. |
| D749,214 S | 2/2016 | Uenishi et al. |
| D749,727 S | 2/2016 | Wapler et al. |
| D751,194 S | 3/2016 | Yu et al. |
| D752,737 S | 3/2016 | Ohashi |
| 9,289,237 B2 | 3/2016 | Woehr et al. |
| 9,308,352 B2 | 4/2016 | Teoh et al. |
| 9,308,354 B2 | 4/2016 | Farrell et al. |
| 9,320,870 B2 | 4/2016 | Woehr |
| D755,368 S | 5/2016 | Efinger et al. |
| 9,352,119 B2 | 5/2016 | Burkholz et al. |
| 9,352,127 B2 | 5/2016 | Yeh et al. |
| 9,352,129 B2 | 5/2016 | Nardeo et al. |
| 9,358,364 B2 | 6/2016 | Isaacson et al. |
| 9,370,641 B2 | 6/2016 | Woehr et al. |
| 9,381,324 B2 | 7/2016 | Fuchs et al. |
| 9,399,116 B2 | 7/2016 | Goral et al. |
| 9,408,569 B2 | 8/2016 | Andreae et al. |
| 9,421,345 B2 | 8/2016 | Woehr et al. |
| 9,427,549 B2 | 8/2016 | Woehr et al. |
| D775,330 S | 12/2016 | Blennow et al. |
| 9,522,254 B2 | 12/2016 | Belson |
| D776,259 S | 1/2017 | Eldredge |
| 9,545,495 B2 | 1/2017 | Goral et al. |
| 9,554,817 B2 | 1/2017 | Goldfarb et al. |
| D779,059 S | 2/2017 | Nino et al. |
| D779,661 S | 2/2017 | McKnight et al. |
| 9,579,486 B2 | 2/2017 | Burkholz et al. |
| 9,586,027 B2 | 3/2017 | Tisci et al. |
| 9,592,367 B2 | 3/2017 | Harding et al. |
| 9,616,201 B2 | 4/2017 | Belson |
| 9,623,210 B2 | 4/2017 | Woehr |
| 9,675,784 B2 | 6/2017 | Belson |
| 9,687,633 B2 | 6/2017 | Teoh |
| D791,311 S | 7/2017 | Yantz |
| 9,707,378 B2 | 7/2017 | Leinsing et al. |
| 9,717,523 B2 | 8/2017 | Feng et al. |
| 9,717,887 B2 | 8/2017 | Tan |
| 9,737,252 B2 | 8/2017 | Teoh et al. |
| 9,750,532 B2 | 9/2017 | Toomey et al. |
| 9,750,928 B2 | 9/2017 | Burkholz et al. |
| 9,757,540 B2 | 9/2017 | Belson |
| 9,764,085 B2 | 9/2017 | Teoh |
| 9,764,117 B2 | 9/2017 | Bierman et al. |
| 9,775,972 B2 | 10/2017 | Christensen et al. |
| 9,782,568 B2 | 10/2017 | Belson |
| 9,789,279 B2 | 10/2017 | Burkholz et al. |
| 9,795,766 B2 | 10/2017 | Teoh |
| 9,844,646 B2 | 12/2017 | Knutsson |
| 9,861,792 B2 | 1/2018 | Hall et al. |
| 9,872,971 B2 | 1/2018 | Blanchard |
| D810,282 S | 2/2018 | Ratjen |
| D815,737 S | 4/2018 | Bergstrom et al. |
| 9,950,139 B2 | 4/2018 | Blanchard et al. |
| 9,962,525 B2 | 5/2018 | Woehr |
| 10,004,878 B2 | 6/2018 | Ishida |
| 10,086,171 B2 | 10/2018 | Belson |
| 10,232,146 B2 | 3/2019 | Braithwaite et al. |
| 10,328,239 B2 | 6/2019 | Belson |
| 10,384,039 B2 | 8/2019 | Ribelin et al. |
| 10,426,931 B2 | 10/2019 | Blanchard et al. |
| D870,271 S | 12/2019 | Kheradpir et al. |
| D870,883 S | 12/2019 | Harding et al. |
| 10,493,262 B2 | 12/2019 | Tran et al. |
| 10,525,236 B2 | 1/2020 | Belson |
| 10,688,280 B2 | 6/2020 | Blanchard et al. |
| 10,688,281 B2 | 6/2020 | Blanchard et al. |
| 10,722,685 B2 | 7/2020 | Blanchard et al. |
| 2001/0014786 A1 | 8/2001 | Greene et al. |
| 2001/0020153 A1 | 9/2001 | Howell |
| 2002/0052576 A1 | 5/2002 | Massengale |
| 2002/0077595 A1 | 6/2002 | Hundertmark et al. |
| 2002/0103446 A1 | 8/2002 | McFann et al. |
| 2002/0107526 A1 | 8/2002 | Greenberg et al. |
| 2002/0128604 A1 | 9/2002 | Nakajima |
| 2002/0165497 A1 | 11/2002 | Greene |
| 2002/0177812 A1 | 11/2002 | Moulton et al. |
| 2003/0032922 A1 | 2/2003 | Moorehead |
| 2003/0032936 A1 | 2/2003 | Lederman |
| 2003/0060760 A1 | 3/2003 | Botich et al. |
| 2003/0073956 A1 | 4/2003 | Hoffman et al. |
| 2003/0120214 A1 | 6/2003 | Howell |
| 2003/0153874 A1 | 8/2003 | Tal |
| 2003/0187396 A1 | 10/2003 | Ponzi |
| 2003/0204186 A1 | 10/2003 | Geistert |
| 2004/0019329 A1 | 1/2004 | Erskine |
| 2004/0034383 A1 | 2/2004 | Belson |
| 2004/0044302 A1 | 3/2004 | Bernard et al. |
| 2004/0044313 A1 | 3/2004 | Nakajima |
| 2004/0092879 A1 | 5/2004 | Kraus et al. |
| 2004/0106903 A1 | 6/2004 | Shue et al. |
| 2004/0111059 A1 | 6/2004 | Howlett et al. |
| 2004/0122373 A1 | 6/2004 | Botich et al. |
| 2004/0176758 A1 | 9/2004 | Yassinzadeh |
| 2004/0193118 A1 | 9/2004 | Bergeron |
| 2004/0215146 A1 | 10/2004 | Lampropoulos et al. |
| 2004/0236288 A1 | 11/2004 | Howell et al. |
| 2004/0243061 A1 | 12/2004 | McGurk |
| 2004/0267204 A1 | 12/2004 | Brustowicz |
| 2005/0004524 A1 | 1/2005 | Newby et al. |
| 2005/0010095 A1 | 1/2005 | Stewart et al. |
| 2005/0020940 A1 | 1/2005 | Opie et al. |
| 2005/0021002 A1 | 1/2005 | Deckman et al. |
| 2005/0027256 A1 | 2/2005 | Barker et al. |
| 2005/0033137 A1 | 2/2005 | Oral et al. |
| 2005/0040061 A1 | 2/2005 | Opie et al. |
| 2005/0075606 A1 | 4/2005 | Botich et al. |
| 2005/0107769 A1 | 5/2005 | Thommen |
| 2005/0119619 A1 | 6/2005 | Haining |
| 2005/0131350 A1 | 6/2005 | Shaw et al. |
| 2005/0165355 A1 | 7/2005 | Fitzgerald |
| 2005/0197623 A1 | 9/2005 | Leeflang et al. |
| 2005/0245847 A1 | 11/2005 | Schaeffer |
| 2005/0256505 A1 | 11/2005 | Long et al. |
| 2005/0273057 A1 | 12/2005 | Popov |
| 2006/0025721 A1 | 2/2006 | Duffy et al. |
| 2006/0079787 A1 | 4/2006 | Whiting et al. |
| 2006/0084964 A1 | 4/2006 | Knudson et al. |
| 2006/0155245 A1 | 7/2006 | Woehr |
| 2006/0161115 A1 | 7/2006 | Fangrow |
| 2006/0167405 A1 | 7/2006 | King et al. |
| 2006/0200080 A1 | 9/2006 | Abulhaj |
| 2006/0229563 A1 | 10/2006 | O'Reagan et al. |
| 2006/0264834 A1 | 11/2006 | Vaillancourt |
| 2007/0043422 A1 | 2/2007 | Shmulewitz et al. |
| 2007/0060999 A1 | 3/2007 | Randall et al. |
| 2007/0083162 A1 | 4/2007 | O'Reagan et al. |
| 2007/0083188 A1 | 4/2007 | Grandt et al. |
| 2007/0100284 A1 | 5/2007 | Leinsing et al. |
| 2007/0123803 A1 | 5/2007 | Fujiwara et al. |
| 2007/0142779 A1 | 6/2007 | Duane et al. |
| 2007/0179446 A1 | 8/2007 | Carrez et al. |
| 2007/0191777 A1 | 8/2007 | King |
| 2007/0193903 A1 | 8/2007 | Opie et al. |
| 2007/0225647 A1 | 9/2007 | Luther et al. |
| 2007/0233007 A1 | 10/2007 | Adams |
| 2007/0244438 A1 | 10/2007 | Perez |
| 2007/0255221 A1 | 11/2007 | Nakajima |
| 2007/0276288 A1 | 11/2007 | Khaw |
| 2008/0039796 A1 | 2/2008 | Nakajima |

(56) References Cited

U.S. PATENT DOCUMENTS

| | | |
|---|---|---|
| 2008/0065011 A1 | 3/2008 | Marchand et al. |
| 2008/0082082 A1 | 4/2008 | Carlyon et al. |
| 2008/0097330 A1 | 4/2008 | King et al. |
| 2008/0108911 A1 | 5/2008 | Palmer et al. |
| 2008/0108944 A1 | 5/2008 | Woehr et al. |
| 2008/0108974 A1 | 5/2008 | Yee Roth |
| 2008/0125709 A1 | 5/2008 | Chang et al. |
| 2008/0131300 A1 | 6/2008 | Junod et al. |
| 2008/0132846 A1 | 6/2008 | Shue et al. |
| 2008/0147010 A1 | 6/2008 | Nakajima et al. |
| 2008/0243165 A1 | 10/2008 | Mauch et al. |
| 2008/0262430 A1 | 10/2008 | Anderson et al. |
| 2008/0262431 A1 | 10/2008 | Anderson et al. |
| 2008/0294111 A1 | 11/2008 | Tal et al. |
| 2008/0300574 A1 | 12/2008 | Belson et al. |
| 2009/0018567 A1 | 1/2009 | Escudero et al. |
| 2009/0030380 A1 | 1/2009 | Binmoeller |
| 2009/0036836 A1 | 2/2009 | Nystrom et al. |
| 2009/0048566 A1 | 2/2009 | Ferguson et al. |
| 2009/0131872 A1 | 5/2009 | Popov |
| 2009/0157006 A1 | 6/2009 | Nardeo et al. |
| 2009/0221961 A1 | 9/2009 | Tal et al. |
| 2009/0292243 A1 | 11/2009 | Harding et al. |
| 2009/0299291 A1 | 12/2009 | Baid |
| 2010/0010441 A1 | 1/2010 | Belson |
| 2010/0010447 A1 | 1/2010 | Luther et al. |
| 2010/0016838 A1 | 1/2010 | Butts et al. |
| 2010/0036331 A1 | 2/2010 | Sen |
| 2010/0056910 A1 | 3/2010 | Yanuma |
| 2010/0057183 A1 | 3/2010 | Mangiardi et al. |
| 2010/0087787 A1 | 4/2010 | Woehr et al. |
| 2010/0094116 A1 | 4/2010 | Silverstein |
| 2010/0094310 A1 | 4/2010 | Warring et al. |
| 2010/0137815 A1 | 6/2010 | Kuracina et al. |
| 2010/0168674 A1 | 7/2010 | Shaw et al. |
| 2010/0204654 A1 | 8/2010 | Mulholland et al. |
| 2010/0204660 A1 | 8/2010 | McKinnon et al. |
| 2010/0204675 A1 | 8/2010 | Woehr et al. |
| 2010/0210934 A1 | 8/2010 | Belson |
| 2010/0238705 A1 | 9/2010 | Kim et al. |
| 2010/0246707 A1 | 9/2010 | Michelitsch |
| 2010/0331732 A1 | 12/2010 | Raulerson et al. |
| 2011/0009827 A1 | 1/2011 | Bierman et al. |
| 2011/0015573 A1 | 1/2011 | Maan et al. |
| 2011/0021994 A1 | 1/2011 | Anderson et al. |
| 2011/0125097 A1 | 5/2011 | Shaw et al. |
| 2011/0137252 A1 | 6/2011 | Oster et al. |
| 2011/0196315 A1 | 8/2011 | Chappel |
| 2011/0207157 A1 | 8/2011 | Gautier et al. |
| 2011/0218496 A1 | 9/2011 | Bierman |
| 2011/0251559 A1 | 10/2011 | Tal et al. |
| 2011/0276002 A1 | 11/2011 | Bierman |
| 2011/0282285 A1 | 11/2011 | Blanchard et al. |
| 2011/0288482 A1 | 11/2011 | Farrell et al. |
| 2011/0306933 A1 | 12/2011 | Djordjevic et al. |
| 2011/0319838 A1 | 12/2011 | Goral et al. |
| 2012/0053523 A1 | 3/2012 | Harding |
| 2012/0071857 A1 | 3/2012 | Goldfarb et al. |
| 2012/0078231 A1 | 3/2012 | Hoshinouchi |
| 2012/0101440 A1 | 4/2012 | Kamen et al. |
| 2012/0123332 A1 | 5/2012 | Erskine |
| 2012/0123354 A1 | 5/2012 | Woehr |
| 2012/0157854 A1 | 6/2012 | Kurrus et al. |
| 2012/0179104 A1 | 7/2012 | Woehr et al. |
| 2012/0184896 A1 | 7/2012 | DeLegge et al. |
| 2012/0197200 A1 | 8/2012 | Belson |
| 2012/0220942 A1 | 8/2012 | Hall et al. |
| 2012/0220956 A1 | 8/2012 | Kuracina et al. |
| 2012/0259293 A1 | 10/2012 | Bialecki et al. |
| 2012/0271232 A1 | 10/2012 | Katsurada et al. |
| 2012/0296282 A1 | 11/2012 | Koehler et al. |
| 2012/0316500 A1 | 12/2012 | Bierman et al. |
| 2012/0323181 A1 | 12/2012 | Shaw et al. |
| 2013/0030391 A1 | 1/2013 | Baid |
| 2013/0158506 A1 | 6/2013 | Harris et al. |
| 2013/0184645 A1 | 7/2013 | Baid |
| 2013/0204206 A1 | 8/2013 | Morgan et al. |
| 2013/0204226 A1 | 8/2013 | Keyser |
| 2013/0218082 A1 | 8/2013 | Hyer et al. |
| 2013/0304030 A1 | 11/2013 | Gray et al. |
| 2013/0310764 A1 | 11/2013 | Burkholz et al. |
| 2013/0324930 A1 | 12/2013 | Fuchs et al. |
| 2014/0012203 A1 | 1/2014 | Woehr et al. |
| 2014/0031752 A1 | 1/2014 | Blanchard et al. |
| 2014/0039461 A1 | 2/2014 | Anderson et al. |
| 2014/0058329 A1 | 2/2014 | Walker et al. |
| 2014/0058336 A1 | 2/2014 | Burkholz et al. |
| 2014/0058357 A1 | 2/2014 | Keyser et al. |
| 2014/0073928 A1 | 3/2014 | Yamashita et al. |
| 2014/0074034 A1 | 3/2014 | Tanabe et al. |
| 2014/0088509 A1 | 3/2014 | Sonderegger et al. |
| 2014/0094774 A1 | 4/2014 | Blanchard |
| 2014/0094836 A1 | 4/2014 | Feng et al. |
| 2014/0114239 A1 | 4/2014 | Dib et al. |
| 2014/0128775 A1 | 5/2014 | Andreae et al. |
| 2014/0135702 A1 | 5/2014 | Woehr et al. |
| 2014/0135703 A1 | 5/2014 | Yeh et al. |
| 2014/0143999 A1 | 5/2014 | Goral et al. |
| 2014/0180250 A1 | 6/2014 | Belson |
| 2014/0188003 A1 | 7/2014 | Belson |
| 2014/0194853 A1 | 7/2014 | Morgan et al. |
| 2014/0214005 A1 | 7/2014 | Belson |
| 2014/0221977 A1 | 8/2014 | Belson |
| 2014/0236099 A1 | 8/2014 | Nakagami et al. |
| 2014/0243734 A1 | 8/2014 | Eubanks et al. |
| 2014/0249488 A1 | 9/2014 | Woehr |
| 2014/0257359 A1 | 9/2014 | Tegels et al. |
| 2014/0276224 A1 | 9/2014 | Ranganathan et al. |
| 2014/0276432 A1 | 9/2014 | Bierman et al. |
| 2014/0276434 A1 | 9/2014 | Woehr et al. |
| 2014/0303561 A1 | 10/2014 | Li |
| 2014/0323988 A1 | 10/2014 | Magnani et al. |
| 2014/0336582 A1 | 11/2014 | Tisci et al. |
| 2014/0357983 A1 | 12/2014 | Toomey et al. |
| 2014/0358123 A1 | 12/2014 | Ueda et al. |
| 2014/0364809 A1 | 12/2014 | Isaacson et al. |
| 2014/0371715 A1 | 12/2014 | Farrell et al. |
| 2014/0371720 A1 | 12/2014 | Urmey |
| 2014/0378867 A1 | 12/2014 | Belson |
| 2015/0025467 A1 | 1/2015 | Woehr |
| 2015/0038909 A1 | 2/2015 | Christensen et al. |
| 2015/0038910 A1 | 2/2015 | Harding et al. |
| 2015/0038943 A1 | 2/2015 | Warring et al. |
| 2015/0051584 A1 | 2/2015 | Korkuch et al. |
| 2015/0080801 A1 | 3/2015 | Tanabe et al. |
| 2015/0080810 A1 | 3/2015 | Henderson et al. |
| 2015/0088095 A1 | 3/2015 | Luther et al. |
| 2015/0119806 A1 | 4/2015 | Blanchard et al. |
| 2015/0119852 A1 | 4/2015 | Wexler |
| 2015/0126932 A1 | 5/2015 | Knutsson |
| 2015/0151086 A1 | 6/2015 | Teoh |
| 2015/0151088 A1 | 6/2015 | Lim et al. |
| 2015/0190168 A1 | 7/2015 | Bierman et al. |
| 2015/0190570 A1 | 7/2015 | Teoh |
| 2015/0190617 A1 | 7/2015 | Anderson et al. |
| 2015/0202414 A1 | 7/2015 | Hwang |
| 2015/0202421 A1 | 7/2015 | Ma et al. |
| 2015/0224267 A1 | 8/2015 | Farrell et al. |
| 2015/0231364 A1 | 8/2015 | Blanchard et al. |
| 2015/0238705 A1 | 8/2015 | Gravesen et al. |
| 2015/0290431 A1 | 10/2015 | Hall et al. |
| 2015/0306347 A1 | 10/2015 | Yagi |
| 2015/0306356 A1 | 10/2015 | Gill |
| 2015/0328434 A1 | 11/2015 | Gaur |
| 2015/0328438 A1 | 11/2015 | Baid |
| 2015/0335858 A1 | 11/2015 | Woehr et al. |
| 2015/0359473 A1 | 12/2015 | Garrett et al. |
| 2016/0008580 A1 | 1/2016 | Woehr et al. |
| 2016/0015943 A1 | 1/2016 | Belson et al. |
| 2016/0015945 A1 | 1/2016 | Warring et al. |
| 2016/0022312 A1 | 1/2016 | Tang et al. |
| 2016/0022963 A1 | 1/2016 | Belson |
| 2016/0030716 A1 | 2/2016 | Mallin et al. |
| 2016/0045715 A1 | 2/2016 | Galgano et al. |

(56) References Cited

U.S. PATENT DOCUMENTS

| | | | |
|---|---|---|---|
| 2016/0106959 A1 | 4/2016 | Woehr | |
| 2016/0114136 A1 | 4/2016 | Woehr | |
| 2016/0114137 A1 | 4/2016 | Woehr et al. | |
| 2016/0158503 A1 | 6/2016 | Woehr | |
| 2016/0158526 A1 | 6/2016 | Woehr | |
| 2016/0175563 A1 | 6/2016 | Woehr et al. | |
| 2016/0184557 A1 | 6/2016 | Call et al. | |
| 2016/0199575 A1 | 7/2016 | Belley et al. | |
| 2016/0206852 A1 | 7/2016 | Morgan et al. | |
| 2016/0206858 A1 | 7/2016 | Ishida | |
| 2016/0220161 A1 | 8/2016 | Goral et al. | |
| 2016/0220786 A1 | 8/2016 | Mitchell et al. | |
| 2016/0256667 A1 | 9/2016 | Ribelin et al. | |
| 2016/0296729 A1 | 10/2016 | Fuchs et al. | |
| 2016/0310704 A1 | 10/2016 | Ng et al. | |
| 2016/0331937 A1 | 11/2016 | Teoh | |
| 2016/0331938 A1 | 11/2016 | Blanchard et al. | |
| 2016/0354580 A1 | 12/2016 | Teoh et al. | |
| 2016/0361490 A1 | 12/2016 | Phang et al. | |
| 2016/0361519 A1 | 12/2016 | Teoh et al. | |
| 2017/0000982 A1 | 1/2017 | Ishida | |
| 2017/0035992 A1 | 2/2017 | Harding et al. | |
| 2017/0043132 A1 | 2/2017 | Ishida | |
| 2017/0087338 A1 | 3/2017 | Belson | |
| 2017/0136217 A1 | 5/2017 | Riesenberger et al. | |
| 2017/0203050 A1 | 7/2017 | Bauer et al. | |
| 2017/0209668 A1 | 7/2017 | Belson | |
| 2017/0246429 A1 | 8/2017 | Tan et al. | |
| 2017/0259036 A1 | 9/2017 | Belson | |
| 2017/0361071 A1 | 12/2017 | Belson | |
| 2018/0028780 A1 | 2/2018 | Blanchard et al. | |
| 2018/0071509 A1 | 3/2018 | Tran et al. | |
| 2018/0099123 A1 | 4/2018 | Woehr | |
| 2018/0133437 A1 | 5/2018 | Blanchard | |
| 2018/0229003 A1 | 8/2018 | Blanchard et al. | |
| 2018/0229004 A1 | 8/2018 | Blanchard et al. | |
| 2019/0022358 A1 | 1/2019 | Belson | |
| 2019/0192829 A1 | 6/2019 | Belson et al. | |
| 2019/0201667 A1 | 7/2019 | Braithwaite et al. | |
| 2019/0240459 A1 | 8/2019 | Belson | |
| 2019/0275303 A1 | 9/2019 | Tran et al. | |
| 2019/0307986 A1 | 10/2019 | Belson | |
| 2019/0351193 A1 | 11/2019 | Hall | |
| 2019/0351196 A1 | 11/2019 | Ribelin et al. | |
| 2020/0001051 A1 | 1/2020 | Huang et al. | |
| 2020/0094037 A1 | 3/2020 | Tran et al. | |
| 2020/0261696 A1 | 8/2020 | Blanchard | |
| 2020/0261703 A1 | 8/2020 | Belson et al. | |
| 2021/0052858 A1 | 2/2021 | Isaacson et al. | |

FOREIGN PATENT DOCUMENTS

| | | | |
|---|---|---|---|
| CN | 1178707 A | | 4/1998 |
| CN | 1319023 A | | 10/2001 |
| CN | 1523970 A | | 8/2004 |
| CN | 1871043 A | | 11/2006 |
| CN | 101242868 A | | 8/2008 |
| CN | 101293122 A | | 10/2008 |
| CN | 101417159 A | | 4/2009 |
| CN | 101784300 A | | 7/2010 |
| CN | 102099075 A | | 6/2011 |
| CN | 102939129 A | | 2/2013 |
| CN | 104689456 A | | 6/2015 |
| CN | 105073174 A | | 11/2015 |
| CN | 105188826 A | | 12/2015 |
| CN | 105705191 A | | 6/2016 |
| DE | 20210394 U1 | | 9/2002 |
| EP | 0314470 | | 5/1989 |
| EP | 417764 A1 | | 3/1991 |
| EP | 475857 A1 | | 3/1992 |
| EP | 515710 A1 | | 12/1992 |
| EP | 567321 A2 | | 10/1993 |
| EP | 652020 A2 | | 5/1995 |
| EP | 747075 A2 | | 12/1996 |
| EP | 750916 A2 | | 1/1997 |
| EP | 778043 A1 | | 6/1997 |
| EP | 800790 A2 | | 10/1997 |
| EP | 832663 A2 | | 4/1998 |
| EP | 910988 A1 | | 4/1999 |
| EP | 942761 A1 | | 9/1999 |
| EP | 1075850 A2 | | 2/2001 |
| EP | 1378263 A2 | | 1/2004 |
| EP | 1418971 A2 | | 5/2004 |
| EP | 1457229 A1 | | 9/2004 |
| EP | 1611916 A1 | | 1/2006 |
| EP | 1907042 A2 | | 4/2008 |
| EP | 2150304 A2 | | 2/2010 |
| EP | 2272432 A1 | | 1/2011 |
| EP | 2569046 A1 | | 3/2013 |
| GB | 2529270 A | | 2/2016 |
| JP | 2003-159334 A | | 6/2003 |
| JP | 2004-130074 A | | 4/2004 |
| JP | 2004-223252 A | | 8/2004 |
| JP | 2005-137888 A | | 6/2005 |
| JP | 2009-500129 A | | 1/2009 |
| JP | 2010-088521 A | | 4/2010 |
| JP | 2013-529111 A | | 7/2013 |
| JP | 2018-118079 A | | 8/2018 |
| WO | 83/01575 A1 | | 5/1983 |
| WO | 1983001575 A1 | | 5/1983 |
| WO | 1992013584 A1 | | 8/1992 |
| WO | 92/22344 A1 | | 12/1992 |
| WO | 1992022344 A1 | | 12/1992 |
| WO | 1995011710 A1 | | 5/1995 |
| WO | 95/19193 A1 | | 7/1995 |
| WO | 1995019193 A1 | | 7/1995 |
| WO | 95/23003 A1 | | 8/1995 |
| WO | 1995023003 A1 | | 8/1995 |
| WO | 96/32981 A1 | | 10/1996 |
| WO | 1996032981 A1 | | 10/1996 |
| WO | 1996040359 A1 | | 12/1996 |
| WO | 97/05912 A2 | | 2/1997 |
| WO | 1997005912 A2 | | 2/1997 |
| WO | 97/21458 A1 | | 6/1997 |
| WO | 1997021458 A1 | | 6/1997 |
| WO | 1997045151 A1 | | 12/1997 |
| WO | 98/24494 A1 | | 6/1998 |
| WO | 1998024494 A1 | | 6/1998 |
| WO | 1998030268 A1 | | 7/1998 |
| WO | 1998053875 A1 | | 12/1998 |
| WO | 1999008742 A1 | | 2/1999 |
| WO | 1999026682 A1 | | 6/1999 |
| WO | 00/06226 A1 | | 2/2000 |
| WO | 00/12160 A1 | | 3/2000 |
| WO | 2000012167 A1 | | 3/2000 |
| WO | 00/47256 A1 | | 8/2000 |
| WO | 00/67829 A1 | | 11/2000 |
| WO | 2001007103 A1 | | 2/2001 |
| WO | 01/26725 A1 | | 4/2001 |
| WO | 2002041932 A2 | | 5/2002 |
| WO | 02/066093 A2 | | 8/2002 |
| WO | 03/11381 A1 | | 2/2003 |
| WO | 03/043686 A1 | | 5/2003 |
| WO | 03/43686 A1 | | 5/2003 |
| WO | 03/047675 A2 | | 6/2003 |
| WO | 03/47675 A2 | | 6/2003 |
| WO | 2004/018031 A2 | | 3/2004 |
| WO | 2005002659 A1 | | 1/2005 |
| WO | 2004106203 A3 | | 3/2005 |
| WO | 2005/074412 A2 | | 8/2005 |
| WO | 2005/087306 A1 | | 9/2005 |
| WO | 2006062996 A2 | | 6/2006 |
| WO | 2007006055 A2 | | 1/2007 |
| WO | 2007/032343 A1 | | 3/2007 |
| WO | 2007094841 A1 | | 8/2007 |
| WO | 2007098355 A1 | | 8/2007 |
| WO | 2007098359 A1 | | 8/2007 |
| WO | 2008005618 A2 | | 1/2008 |
| WO | 2008030999 A2 | | 3/2008 |
| WO | 2008/131300 A2 | | 10/2008 |
| WO | 2008137956 A2 | | 11/2008 |
| WO | 2009/001309 A1 | | 12/2008 |
| WO | 2008147600 A1 | | 12/2008 |
| WO | 2009031161 A1 | | 3/2009 |

(56) References Cited

FOREIGN PATENT DOCUMENTS

| | | | |
|---|---|---|---|
| WO | 2009114837 A2 | 9/2009 |
| WO | 2009/124990 A1 | 10/2009 |
| WO | 2010015676 A1 | 2/2010 |
| WO | 2010/048449 A2 | 4/2010 |
| WO | 2010/132608 A2 | 11/2010 |
| WO | 2011036574 A1 | 3/2011 |
| WO | 2011143621 A1 | 11/2011 |
| WO | 2012106266 A1 | 8/2012 |
| WO | 2012154277 A1 | 11/2012 |
| WO | 2012174109 A1 | 12/2012 |
| WO | 2013119557 A1 | 8/2013 |
| WO | 2013126446 A1 | 8/2013 |
| WO | 2013187827 A1 | 12/2013 |
| WO | 2014006403 A1 | 1/2014 |
| WO | 2014029424 A1 | 2/2014 |
| WO | 2014074417 A2 | 5/2014 |
| WO | 2014081942 A1 | 5/2014 |
| WO | 2014/123848 A1 | 8/2014 |
| WO | 2014120741 A1 | 8/2014 |
| WO | 2014133617 A1 | 9/2014 |
| WO | 2014140257 A1 | 9/2014 |
| WO | 2014140265 A1 | 9/2014 |
| WO | 2014/165783 A1 | 10/2014 |
| WO | 2014158908 A1 | 10/2014 |
| WO | 2014182421 A1 | 11/2014 |
| WO | 2014197656 A1 | 12/2014 |
| WO | 2014204593 A1 | 12/2014 |
| WO | 2015017136 A1 | 2/2015 |
| WO | 2015024904 A1 | 2/2015 |
| WO | 2015035393 A1 | 3/2015 |
| WO | 2015058136 A1 | 4/2015 |
| WO | 15108913 A1 | 7/2015 |
| WO | 2015/168655 A2 | 11/2015 |
| WO | 15164912 A1 | 11/2015 |
| WO | 2016/037127 A1 | 3/2016 |
| WO | 16178974 A1 | 11/2016 |
| WO | 2018/049413 A1 | 3/2018 |
| WO | 2018170349 A1 | 9/2018 |
| WO | 2019173641 A1 | 9/2019 |

OTHER PUBLICATIONS

EP 07783404.2 filed Jan. 19, 2009 Office Action dated Apr. 16, 2019.
EP 16797047.4 filed Dec. 6, 2017 Supplemental European Search Report dated Jan. 9, 2019.
JP 2016-563441 filed Oct. 19, 2016 Office Action dated Jan. 25, 2019.
JP 2018-039302 filed Mar. 6, 2018 Office Action dated Feb. 20, 2019.
U.S. Appl. No. 14/585,800, filed Dec. 30, 2014 Notice of Allowance dated Feb. 25, 2019.
U.S. Appl. No. 15/154,384, filed May 13, 2016 Restriction Requirment dated Jan. 25, 2019.
U.S. Appl. No. 15/154,808, filed May 13, 2016 Notice of Allowance dated Apr. 16, 2019.
U.S. Appl. No. 15/702,537, filed Sep. 12, 2017 Final Office Action dated Mar. 8, 2019.
U.S. Appl. No. 15/154,384, filed May 13, 2016 Final Office Action dated Nov. 27, 2019.
U.S. Appl. No. 15/727,528, filed Oct. 6, 2017 Final Office Action dated Jan. 28, 2020.
U.S. Appl. No. 15/951,931, filed Apr. 12, 2018 Non-Final Office Action dated Nov. 19, 2019.
EP 16797029.2 filed Nov. 21, 2017 Office Action dated Mar. 27, 2020.
U.S. Appl. No. 15/727,528, filed Oct. 6, 2017 Notice of Allowance dated Mar. 27, 2020.
U.S. Appl. No. 15/869,872, filed Jan. 12, 2018 Non-Final Office Action dated Apr. 10, 2020.
U.S. Appl. No. 15/951,931, filed Apr. 12, 2018 Notice of Allowance dated Feb. 20, 2020.
U.S. Appl. No. 15/951,931, filed Apr. 12, 2018 Notice of Allowability dated Apr. 16, 2020.
U.S. Appl. No. 15/951,954, filed Apr. 12, 2018 Notice of Allowance dated Feb. 23, 2020.
U.S. Appl. No. 15/951,954, filed Apr. 12, 2018 Notice of Allowability dated Apr. 7, 2020.
U.S. Appl. No. 16/138,523, filed Sep. 21, 2018 Notice of Allowance dated Mar. 26, 2020.
U.S. Appl. No. 29/654,521, filed Jun. 25, 2018 Restriction Requirement dated Apr. 8, 2020.
U.S. Appl. No. 29/654,527, filed Jun. 25, 2018 Restriction Requirement dated Mar. 10, 2020.
EP 12782187.4 filed Sep. 10, 2013 Office Action dated Nov. 28, 2018.
PCT/US2017/051214 filed Sep. 12, 2017 International Search Report and Written Opinion dated Nov. 13, 2017.
SG 11201709185X filed Nov. 8, 2017 Office Action dated Oct. 5, 2018.
SG 11201709193S filed Nov. 8, 2017 Office Action dated Oct. 5, 2018.
U.S. Appl. No. 14/846,387, filed Sep. 4, 2015 Notice of Allowance dated Oct. 29, 2018.
U.S. Appl. No. 14/866,441, filed Sep. 25, 2015 Notice of Allowance dated Oct. 17, 2018.
U.S. Appl. No. 15/154,808, filed May 13, 2016 Advisory Action dated Oct. 26, 2018.
U.S. Appl. No. 15/377,880, filed Dec. 13, 2016 Final Office Action dated Oct. 19, 2018.
U.S. Appl. No. 15/481,773, filed Apr. 7, 2017 Final Office Action dated Jan. 10, 2019.
U.S. Appl. No. 15/702,537, filed Sep. 12, 2017 Non-Final Office Action dated Nov. 29, 2018.
U.S. Appl. No. 14/585,800, filed Dec. 30, 2014 Non-Final Office Action dated May 16, 2016.
U.S. Appl. No. 14/585,800, filed Dec. 30, 2014 Non-Final Office Action dated Nov. 29, 2016.
U.S. Appl. No. 14/585,800, filed Dec. 30, 2014 Non-Final Office Action dated Nov. 3, 2017.
U.S. Appl. No. 14/585,800, filed Dec. 30, 2014 Non-Final Office Action dated Oct. 8, 2015.
U.S. Appl. No. 14/585,800, filed Dec. 30, 2014 Notice of Allowance dated Jul. 3, 2017.
U.S. Appl. No. 14/702,580, filed May 1, 2015 Advisory Action dated Nov. 13, 2017.
U.S. Appl. No. 14/702,580, filed May 1, 2015 Final Office Action dated Sep. 1, 2017.
U.S. Appl. No. 14/702,580, filed May 1, 2015 Non-Final Office Action dated May 3, 2017.
U.S. Appl. No. 14/702,580, filed May 1, 2015 Notice of Allowance dated Dec. 8, 2017.
U.S. Appl. No. 14/750,658, filed Jun. 25, 2016 Non-Final Office Action dated Mar. 9, 2017.
U.S. Appl. No. 14/750,658, filed Jun. 25, 2016 Notice of Allowance dated Jul. 20, 2017.
U.S. Appl. No. 14/846,387, filed Sep. 4, 2015 Non-Final Office Action dated Sep. 22, 2017.
U.S. Appl. No. 14/866,441, filed Sep. 25, 2015 Advisory Action dated Dec. 22, 2016.
U.S. Appl. No. 14/866,441, filed Sep. 25, 2015 Final Office Action dated Sep. 23, 2016.
U.S. Appl. No. 14/866,441, filed Sep. 25, 2015 Non-Final Office Action dated Apr. 7, 2017.
U.S. Appl. No. 14/866,441, filed Sep. 25, 2015 Non-Final Office Action dated Mar. 14, 2016.
U.S. Appl. No. 14/866,738, filed Sep. 25, 2015 Final Office Action dated Feb. 24, 2017.
U.S. Appl. No. 14/866,738, filed Sep. 25, 2015 Non-Final Office Action dated Nov. 6, 2017.
U.S. Appl. No. 14/866,738, filed Sep. 25, 2015 Non-Final Office Action dated Oct. 31, 2016.
U.S. Appl. No. 14/866,738, filed Sep. 25, 2015 Notice of Panel Decision dated Jun. 23, 2017.

(56) References Cited

OTHER PUBLICATIONS

U.S. Appl. No. 14/876,735, filed Oct. 6, 2015 Non-Final Office Action dated Mar. 30, 2017.
U.S. Appl. No. 29/536,043, filed Aug. 12, 2015 Non-Final Office Action dated Aug. 31, 2017.
U.S. Appl. No. 29/545,436, filed Nov. 12, 2015 Non-Final Office Action dated Sep. 12, 2017.
Waltimire, B. and Rasor, J.S., Midline catheter: Virtually bloodless insertion technique and needle safety tube minimize potential for transmission of bloodborne disease. Sponsored by national Foundation for Infectious Diseases. 5th National forum on AIDS, Hepatitis, and other blood-borne diseases. Atlanta, GA, Mar. 1992.
Office action dated Nov. 4, 2013 for U.S. Appl. No. 12/307,519.
Office action dated Mar. 12, 2015 for U.S. Appl. No. 11/577,491.
PCT/CN2017/075370 filed Mar. 1, 2017 International Search Report and Written Opinion dated Nov. 30, 2017.
PCT/US15/28950 filed May 1, 2015 International Search Report and Written Opinion dated Oct. 19, 2015.
PCT/US2008/062954 filed May 7, 2008 International search report and written opinion dated Jan. 16, 2009.
PCT/US2011/036530 filed May 13, 2011 International Search Report dated Oct. 6, 2011.
PCT/US2011/036530 filed May 13, 2011 Written Opinion of the International Searching Authority dated Oct. 6, 2011.
PCT/US2012/026618 International Preliminary Report on Patentability dated Aug. 27, 2013.
PCT/US2012/026618 International Search Report and Written Opinion dated Jun. 25, 2012.
PCT/US2013/073577 filed Dec. 6, 2013 International Search Report and Written Opinion dated Feb. 24, 2014.
PCT/US2014/013557 filed Jan. 29, 2014 International search report and written opinion dated Apr. 14, 2014.
PCT/US2015/048676 filed Sep. 4, 2015 International search report and written opinion dated Dec. 4, 2015.
PCT/US2016/032449 filed May 13, 2016 International Search Report and Written Opinion dated Oct. 5, 2016.
PCT/US2016/032534 filed May 13, 2016 International Search Report and Written Opinion dated Oct. 5, 2016.
PR Newswire, Luther Medical Products, Inc. Receives Approval to Supply Improved Neonatal Product to Japan, Aug. 20, 1998.
Rasor, Julia S, Review of Catheter-related infection rates: comparison of conventional catheter materials with Aquavene®, JVAN vol. 1, No. 3, Spring 1991.
U.S. Appl. No. 12/598,053, filed Apr. 20, 2010 Notice of allowance dated Jan. 16, 2014.
U.S. Appl. No. 12/598,053, filed Apr. 20, 2010 Office action dated Aug. 28, 2013.
U.S. Appl. No. 12/598,053, filed Apr. 20, 2010 Office action dated Dec. 4, 2012.
U.S. Appl. No. 12/598,053, filed Apr. 20, 2010 Office action dated May 8, 2013.
U.S. Appl. No. 12/598,053, filed Apr. 20, 2010 Office action dated Oct. 24, 2013.
U.S. Appl. No. 13/107,781, filed May 13, 2011 Final Office Action dated Jul. 18, 2014.
U.S. Appl. No. 13/107,781, filed May 13, 2011 Non-Final Office Action dated Dec. 30, 2013.
U.S. Appl. No. 13/405,096, filed Feb. 24, 2012 Advisory Action dated Apr. 18, 2014.
U.S. Appl. No. 13/405,096, filed Feb. 24, 2012 Final Office Action dated Jan. 31, 2014.
U.S. Appl. No. 13/405,096, filed Feb. 24, 2012 Non-Final Office Action dated Aug. 20, 2013.
U.S. Appl. No. 13/405,096, filed Feb. 24, 2012 Non-Final Office Action dated Nov. 18, 2014.
U.S. Appl. No. 13/405,096, filed Feb. 24, 2012 Notice of Allowance dated Mar. 11, 2015.
U.S. Appl. No. 14/044,623, filed Oct. 2, 2013 Notice of Allowance dated Nov. 6, 2014.
U.S. Appl. No. 14/099,050, filed Dec. 6, 2013 Advisory Action dated Jun. 1, 2017.
U.S. Appl. No. 14/099,050, filed Dec. 6, 2013 Final Office Action dated Jan. 30, 2017.
U.S. Appl. No. 14/099,050, filed Dec. 6, 2013 Non-Final Office Action dated Dec. 22, 2015.
U.S. Appl. No. 14/099,050, filed Dec. 6, 2013 Non-Final Office Action dated Jul. 19, 2016.
U.S. Appl. No. 14/099,050, filed Dec. 6, 2013 Notice of Allowance dated Sep. 14, 2017.
U.S. Appl. No. 14/099,050, filed Dec. 6, 2013 Notice of Panel Decision dated Aug. 1, 2017.
U.S. Appl. No. 14/167,149, filed Jan. 29, 2014 Non-Final Office Action dated Oct. 21, 2015.
U.S. Appl. No. 14/167,149, filed Jan. 29, 2014 Notice of Allowance dated Jul. 6, 2016.
U.S. Appl. No. 14/174,071, filed Feb. 6, 2014 Final Office Action dated Dec. 2, 2016.
U.S. Appl. No. 14/174,071, filed Feb. 6, 2014 Non-Final Office Action dated Jul. 29, 2016.
U.S. Appl. No. 14/174,071, filed Feb. 6, 2014 Non-Final Office Action dated Mar. 31, 2016.
U.S. Appl. No. 14/192,541, filed Feb. 27, 2014 Non-Final Office Action dated Jul. 20, 2016.
U.S. Appl. No. 14/192,541, filed Feb. 27, 2014 Notice of Allowance dated Dec. 6, 2016.
U.S. Appl. No. 14/192,541, filed Feb. 27, 2014 Notice of Corrected Allowability dated Mar. 8, 2017.
U.S. Appl. No. 14/250,093, filed Apr. 10, 2014 Advisory Action dated May 19, 2017.
U.S. Appl. No. 14/250,093, filed Apr. 10, 2014 Final Office Action dated Mar. 9, 2017.
U.S. Appl. No. 14/250,093, filed Apr. 10, 2014 Final Office Action dated Nov. 6, 2017.
U.S. Appl. No. 14/250,093, filed Apr. 10, 2014 Non-Final Office Action dated Nov. 16, 2016.
U.S. Appl. No. 14/250,093, filed Apr. 10, 2014 Panel Decision dated Jul. 14, 2017.
U.S. Appl. No. 14/477,717, filed Sep. 4, 2014, Notice of allowance dated Feb. 17, 2015.
U.S. Appl. No. 14/477,717, filed Sep. 4, 2014, Office action dated Dec. 18, 2014.
CN 201580022407.7 filed Nov. 2, 2016 Office Action dated Sep. 16, 2019.
EP 19181963.0 filed Jun. 24, 2019 Extended European Search Report dated Jul. 16, 2019.
U.S. Appl. No. 15/154,384, filed May 13, 2016 Non-Final Office Action dated Jun. 28, 2019.
U.S. Appl. No. 15/608,802, filed May 30, 2017 Non-Final Office Action dated Jun. 6, 2019.
U.S. Appl. No. 15/702,537, filed Sep. 12, 2017 Notice of Allowance dated Jul. 31, 2019.
U.S. Appl. No. 15/727,528, filed Oct. 6, 2017 Non-Final Office Action dated Sep. 20, 2019.
U.S. Appl. No. 15/727,528, filed Oct. 6, 2017 Restriction Requirement dated Aug. 7, 2019.
U.S. Appl. No. 15/951,954, filed Apr. 12, 2018 Non-Final Office Action dated Nov. 4, 2019.
CN 201380073657.4 filed Aug. 21, 2015 Office Action dated Mar. 2, 2018.
CN 201510079782.7 filed Feb. 13, 2015 Office Action dated Feb. 5, 2018.
EP 07783404.2 filed Jan. 19, 2009 Office Action dated Mar. 7, 2018.
EP 12782187.4 filed Sep. 10, 2013 Office Action dated Apr. 24, 2018.
EP 16797029.2 filed Nov. 21, 2017 Extended European Search Report dated May 3, 2018.
JP 2015-560173 filed Aug. 28, 2015 Office Action dated Aug. 2, 2018.
JP 2016-107046 filed May 30, 2016 Office Action dated Nov. 7, 2017.
RU 2017141812 filed Nov. 30, 2017 Office Action dated Jan. 31, 2018.

(56) References Cited

OTHER PUBLICATIONS

U.S. Appl. No. 14/250,093, filed Apr. 10, 2014 Examiner's Answer dated Jun. 20, 2018.
U.S. Appl. No. 14/585,800, filed Dec. 30, 2014 Final Office Action dated May 11, 2018.
U.S. Appl. No. 14/846,387, filed Sep. 4, 2015 Advisory Action dated May 10, 2018.
U.S. Appl. No. 14/846,387, filed Sep. 4, 2015 Final Office Action dated Mar. 22, 2018.
U.S. Appl. No. 14/866,441, filed Sep. 25, 2015 Final Office Action dated Jun. 5, 2018.
U.S. Appl. No. 15/154,808, filed May 13, 2016 Final Office Action dated Aug. 16, 2018.
U.S. Appl. No. 15/154,808, filed May 13, 2016 Non-Final Office Action dated Apr. 6, 2018.
U.S. Appl. No. 15/154,808, filed May 13, 2016 Restriction Requirement dated Jan. 3, 2018.
U.S. Appl. No. 15/377,880, filed Dec. 13, 2016 Non-Final Office Action dated May 14, 2018.
U.S. Appl. No. 15/481,773, filed Apr. 7, 2017 Non-Final Office Action dated Jun. 29, 2018.
U.S. Appl. No. 15/692,915, filed Aug. 31, 2017 Non-Final Office Action dated Jan. 29, 2018.
U.S. Appl. No. 29/536,043, filed Aug. 12, 2015 Final Office Action dated Mar. 26, 2018.
U.S. Appl. No. 29/545,436, filed Nov. 12, 2015 Final Office Action dated Mar. 26, 2018.
Access Scientific, The PICC Wand® Product Data Sheet, Revision F, May 22, 2012.
Access Scientific, The Powerwand® Extended Dwell Catheter Brochure (http://accessscientific.com/media/4Fr-POWERWAND-Brochure.pdf) last accessed Sep. 25, 2015.
BD Angiocath™ Autoguard™ Shielded IV Catheter Brochure, © 2001.
BD Medical Systems, I.V. Catheter Family Brochure (2006).
BD Saf-T-Intima™ Integrated Safety IV Catheter Brochure, © 2001.
Becton Dickinson, Insyte® AutoGuard™ Shielded I.V. Catheter Brochure, 1998.
CA 2,799,360 filed May 13, 2011 Office Action dated Jun. 7, 2017.
CN 201180029526.7 filed Dec. 14, 2012 First Office Action dated Apr. 21, 2014.
CN 2012800008866.6 filed Aug. 14, 2013 Second Office Action dated Aug. 17, 2015.
CN 201280008866.6 filed Aug. 14, 2013 First Office Action dated Dec. 31, 2014.
CN 201280008866.6 filed Aug. 14, 2013 Third Office Action dated Jan. 25, 2016.
CN 201380073657.4 filed Aug. 21, 2015 Office Action dated Jun. 28, 2017.
CN 201480019467.9 filed Sep. 29, 2015 Office Action dated Apr. 6, 2017.
CN 201510079782.7 filed Feb. 13, 2015 Office Action dated Dec. 30, 2016.
CN 201510079782.7 filed Feb. 13, 2015 Office Action dated Sep. 19, 2017.
Cook Medical "Lunderquist Extra-Stiff wire guide" (2012).
Endovascular Today "Coiled Stainless Steel Guidewires" Buyer's Guide pp. 13-20, (2012).
EP 10075422.5 filed Jul. 5, 2008 European search report and written opinion dated Dec. 1, 2010.
EP 11781384.0 filed Sep. 21, 2012 Extended European Search Report dated Oct. 31, 2017.
EP 12782187.4 filed Sep. 10, 2013 European search report and written opinion dated Aug. 30, 2016.
EP 12782187.4 filed Sep. 10, 2013 European search report and written opinion dated Dec. 17, 2015.
EP 13876666.2 filed Sep. 7, 2015 Extended European Search Report dated Sep. 20, 2016.
EP 15785819.2 filed Dec. 2, 2016 Extended European Search Report dated Dec. 4, 2017.
European office action dated Apr. 21, 2008 for EP Application No. 06800027.2.
European office action dated Aug. 6, 2012 for EP Application No. 07783404.2.
European office action dated Oct. 5, 2010 for EP Application No. 07783404.2.
European search report and opinion dated Jul. 10, 2009 for EP Application No. 07783404.2.
Hadaway, Lynn C., A Midline Alternative to Central and Peripheral Venous Access, Caring Magazine, May 1990, pp. 45-50.
International search report and written opinion dated Apr. 2, 2012 for PCT/US2012/023192.
International search report and written opinion dated Jun. 1, 2007 for PCT/US2006/026671.
International search report and written opinion dated Oct. 23, 2008 for PCT/US2007/068393.
JP 2013-510353 filed Oct. 31, 2012 First Office Action dated Feb. 19, 2015.
JP 2013-510353 filed Oct. 31, 2012 Office Action dated Dec. 15, 2016.
JP 2013-510353 filed Oct. 31, 2012 Second Office Action dated Jan. 28, 2016.
JP 2015-560173 filed Aug. 28, 2015 Office Action dated Sep. 19, 2017.
JP 2016-107046 filed May 30, 2016 Office Action dated Apr. 26, 2017.
JP 2016-107046 filed May 30, 2016 Office Action dated Jul. 28, 2016.
Menlo Care, Landmark™ Aquavene® Catheters Brochure, 1992.
Menlo Care, Landmark® Midline Catheter Maintenance and Reference Guide (1993).
Menlo Care, Landmark® Midline Catheters Brochure, 1991.
Menlo Care, Landmark® Venous Access Device Insertion Instructions (1992).
Menlo Care, Publications on Aquavene® Technology, Aug. 1992.
Notice of allowance dated Jan. 29, 2014 for U.S. Appl. No. 12/307,519.
Notice of allowance dated Jun. 10, 2015 for U.S. Appl. No. 11/577,491.
Office action dated Mar. 10, 2011 for U.S. Appl. No. 12/307,519.
Office action dated Mar. 15, 2011 for U.S. Appl. No. 11/577,491.
Office action dated Mar. 27, 2013 for U.S. Appl. No. 13/358,099.
Office action dated Aug. 2, 2010 for U.S. Appl. No. 11/577,491.
Office action dated Aug. 18, 2014 for U.S. Appl. No. 11/577,491.
Office action dated Oct. 25, 2010 for U.S. Appl. No. 12/307,519.
EP17849786.3 filed Apr. 12, 2019 Extended European Search Report dated May 13, 2020.
PCT/US2019/021231 filed Mar. 7, 2019 International Search Report and Written Opinion, dated Jun. 27, 2019.
U.S. Appl. No. 14/250,093, filed Apr. 10, 2014 Notice of Allowance dated Aug. 19, 2020.
U.S. Appl. No. 14/250,093, filed Apr. 10, 2014 Patent Board Decision dated Jun. 8, 2020.
U.S. Appl. No. 14/866,738, filed Sep. 25, 2015 Notice of Allowance dated Sep. 24, 2020.
U.S. Appl. No. 14/866,738, filed Sep. 25, 2015 Patent Board Decision dated Jul. 13, 2020.
U.S. Appl. No. 15/154,384, filed May 13, 2016 Non-Final Office Action dated Jun. 26, 2020.
U.S. Appl. No. 15/869,872, filed Jan. 12, 2018 Advisory Action dated Sep. 23, 2020.
U.S. Appl. No. 15/869,872, filed Jan. 12, 2018 Final Office Action dated Jun. 25, 2020.
U.S. Appl. No. 16/292,076, filed Mar. 4, 2019 Non-Final Office Action dated Aug. 10, 2020.
U.S. Appl. No. 16/295,906, filed Mar. 7, 2019 Non-Final Office Action dated Sep. 4, 2020.
U.S. Appl. No. 29/654,521, filed Jun. 25, 2018 Notice of Allowability dated Sep. 30, 2020.
U.S. Appl. No. 29/654,521, filed Jun. 25, 2018 Notice of Allowance dated Aug. 17, 2020.

(56) References Cited

OTHER PUBLICATIONS

U.S. Appl. No. 29/654,527, filed Jun. 25, 2018 Notice of Allowability dated Sep. 30, 2020.
U.S. Appl. No. 29/654,527, filed Jun. 25, 2018 Notice of Allowance dated Aug. 18, 2020.
U.S. Appl. No. 29/658,136, filed Jul. 27, 2018 Non-Final Office Action dated Sep. 9, 2020.
U.S. Appl. No. 29/658,136, filed Jul. 27, 2018 Restriction Requirement dated May 11, 2020.
U.S. Appl. No. 15/154,384, filed May 13, 2016 Final Office Action dated Dec. 24, 2020.
U.S. Appl. No. 15/154,384, filed May 13, 2016 Notice of Allowance dated Mar. 17, 2021.
U.S. Appl. No. 16/292,076, filed Mar. 4, 2019 Corrected Notice of Allowance dated Feb. 25, 2021.
U.S. Appl. No. 16/292,076, filed Mar. 4, 2019 Notice of Allowance dated Feb. 4, 2021.
U.S. Appl. No. 16/295,906, filed Mar. 7, 2019 Final Office Action dated Dec. 22, 2020.
U.S. Appl. No. 16/295,906, filed Mar. 7, 2019 Notice of Allowance dated Mar. 4, 2021.
U.S. Appl. No. 16/296,087, filed Mar. 7, 2019 Restriction Requirement dated Feb. 8, 2021.
U.S. Appl. No. 16/529,602, filed Aug. 1, 2019 Notice of Allowance dated Jan. 19, 2021.
U.S. Appl. No. 29/658,136, filed Jul. 27, 2018 Notice of Allowance dated Mar. 23, 2021.
U.S. Appl. No. 16/296,087, filed Mar. 7, 2019 Non-Final Office Action dated Mar. 26, 2021.
U.S. Appl. No. 16/490,023, filed Aug. 29, 2019 Restriction Requirement dated May 4, 2021.
U.S. Appl. No. 15/154,384, filed May 13, 2016 Notice of Allowance dated Apr. 29, 2021.
U.S. Appl. No. 16/389,719, filed Apr. 19, 2019 Final Office Action dated Jun. 14, 2021.

* cited by examiner

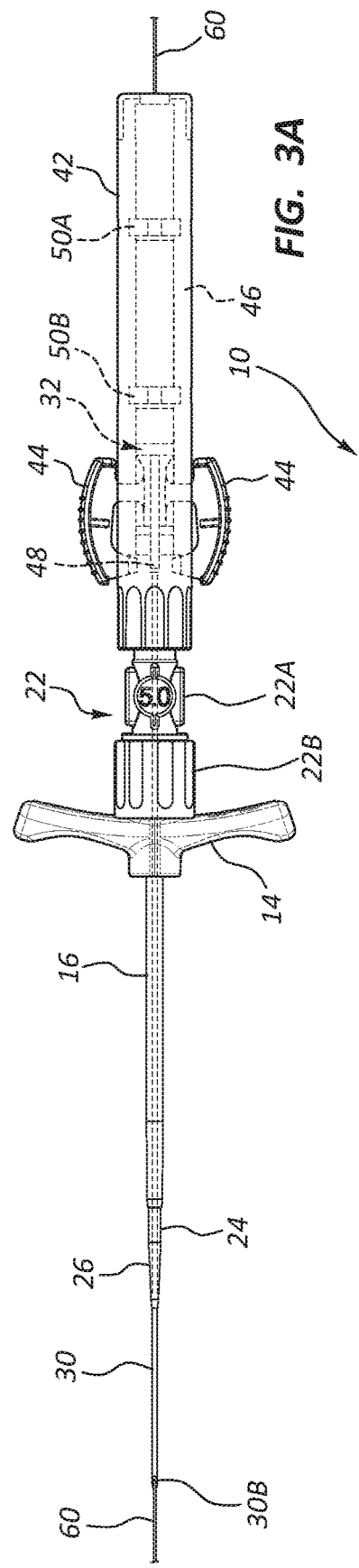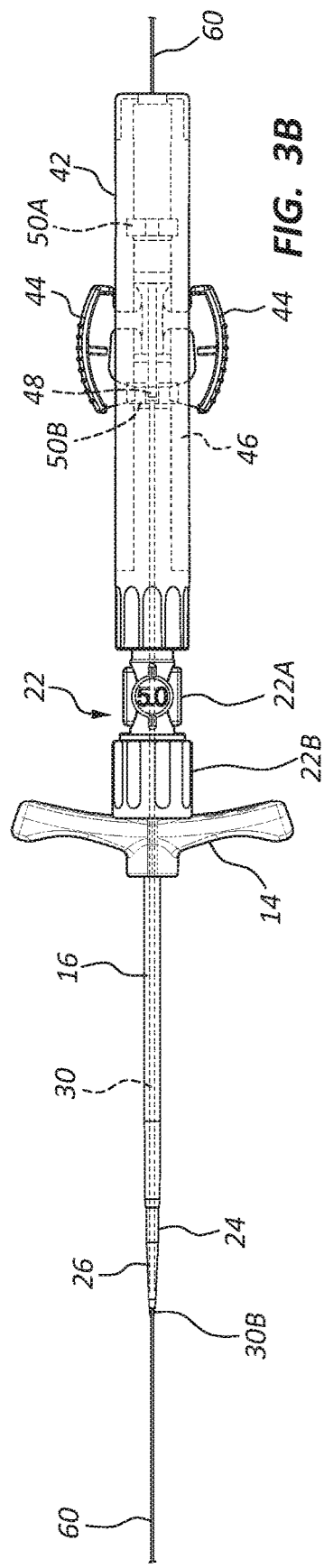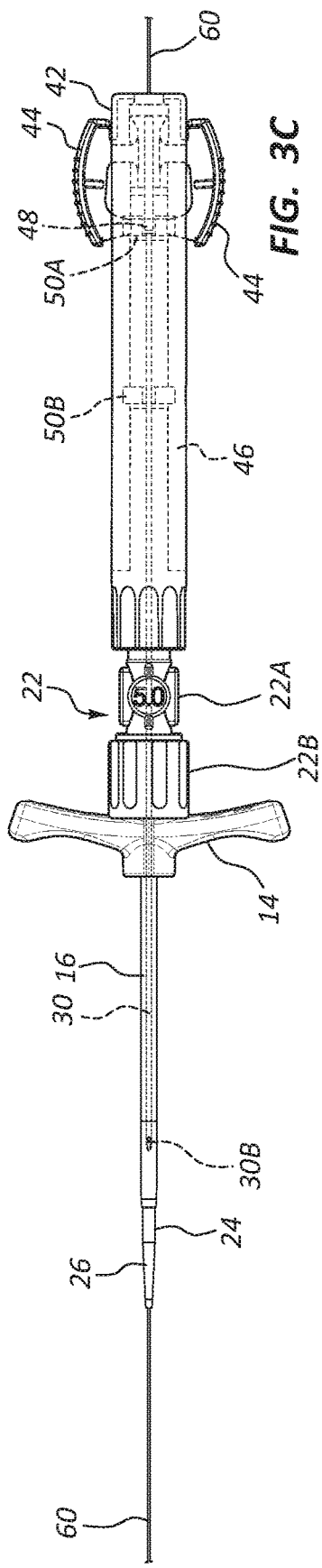

MEDICAL COMPONENT INSERTION DEVICE INCLUDING A RETRACTABLE NEEDLE

CROSS-REFERENCE TO RELATED APPLICATIONS

This application is a division of U.S. patent application Ser. No. 14/750,658, filed Jun. 25, 2015, now U.S. Pat. No. 9,861,792, which is a division of U.S. patent application Ser. No. 13/405,096, filed Feb. 24, 2012, now U.S. Pat. No. 9,095,683, which claims the benefit of U.S. Provisional Patent Application No. 61/446,817, filed Feb. 25, 2011, and titled "Introducer Assembly Including a Retractable Needle," each of which is incorporated herein by reference in its entirety.

BRIEF SUMMARY

Briefly summarized, embodiments of the present invention are directed to an insertion device for use in assisting with the placement of a medical device within the body of a patient. For example, the insertion device can be employed to assist with the placement of an introducer, which provides a conduit into the body to enable insertion of a catheter.

In one embodiment, the insertion device comprises a needle that is removably disposed within a bore defined by the medical device, and a needle retraction assembly. The needle retraction assembly is capable of positioning the needle in any one of a first position wherein a distal tip of the needle is disposed a predetermined distance distal to a distal end of the medical device, a second position wherein the needle distal tip is disposed distal but proximate to the distal end of the medical device, and a third position wherein the needle distal tip is retracted within the medical device bore.

As mentioned, in one embodiment the medical device is an introducer assembly that includes a dilator coaxially disposed within a sheath, with the needle disposed within a bore defined by the dilator. The needle retraction assembly can include a housing that is releasably attached to a proximal end of the dilator. A hub of the needle can be slidably disposed within the housing to enable manual movement of the needle between any of the three needle positions described above. As will be seen, each of the three needle positions facilitates simple insertion of the medical device into the patient while minimizing trauma thereto.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIGS. 3A-3C show the insertion device of FIGS. 1A-1C in various configurations;

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments of the present invention are generally directed to an insertion device for use in assisting with the placement of a medical device within the body of a patient. For example, the insertion device can be employed to assist with the placement of an introducer, which provides a conduit into the body of the patient to enable insertion of a catheter therethrough. In another example, the insertion device can be used to place a catheter directly into the patient's body without the use of an introducer. Other medical devices can also be placed with the insertion device described herein. In one embodiment, the insertion device includes a needle that is positionable in one of three or more positions during use of the device so as to ease insertion of the medical device into the body.

Figure 1A:
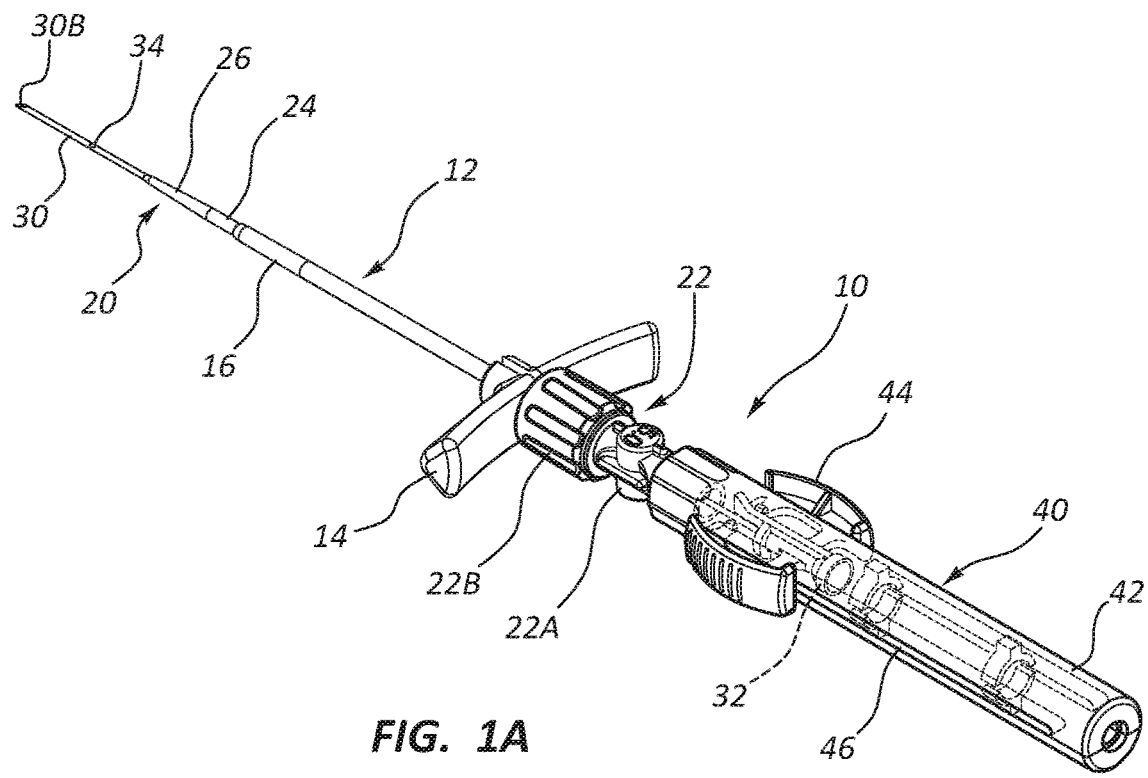
FIGS. 1A-1C are various views of an insertion device according to one embodiment.
Figure 1B:
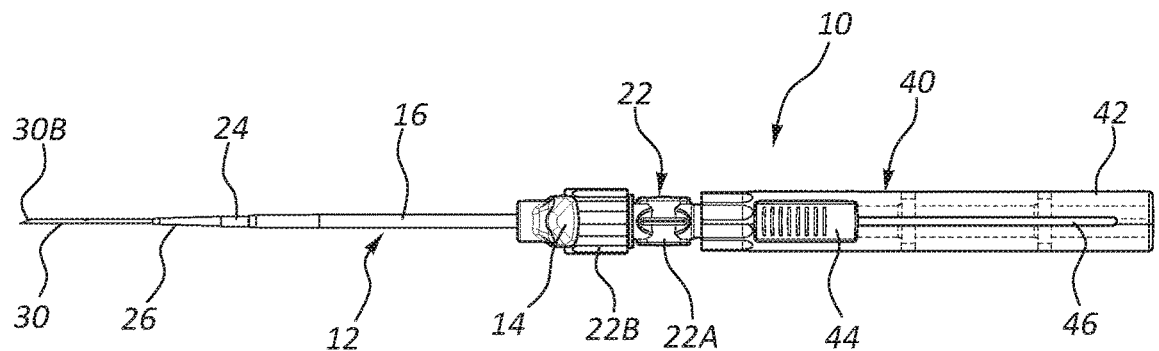
Figure 1C:
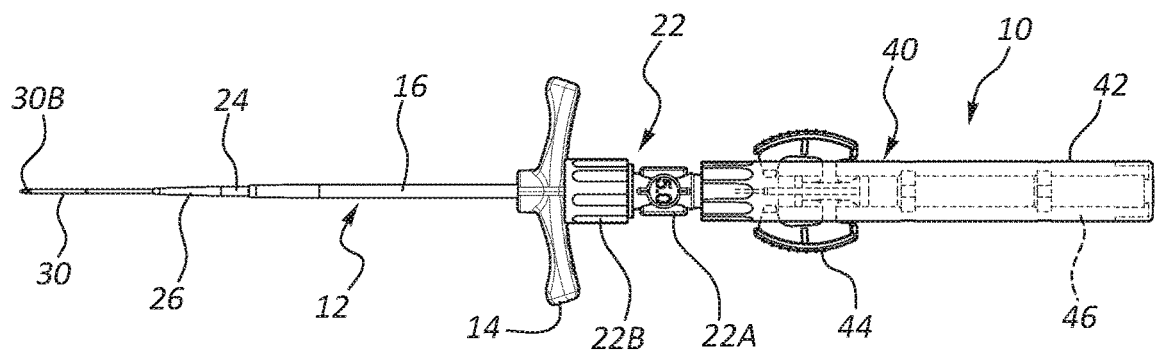

Reference is first made to FIGS. 1A-1C, which show various details regarding an insertion device, generally designated at 10, according to one embodiment. As shown, the device 10 is initially mated with an introducer 12, which in turn includes an introducer hub 14 and a sheath body ("sheath") 16 extending distal from the hub. The introducer hub 14 defines a handle for use in manipulating the introducer 12 during use. The introducer hub 14 and the sheath 16 of the introducer 12 together define a longitudinal bore. Though configured to be splittable here, the introducer in other embodiments need not be splittable.

A dilator 20 is coaxially disposed within the bore of the introducer 12. As shown, the dilator 20 includes a hub 22 and a body 24 extending distally from the hub. The dilator hub 22 and body 24 together define a bore therethrough for the passage of an optional guidewire. The dilator hub 22 defines a base portion 22A and a cap portion 22B. The cap portion 22B is configured to threadably engage the hub 14 of the introducer 12 so as to releasably mate the introducer and the dilator 20 as shown in FIGS. 1A-1C. In this mated configuration, it is seen that a tapered distal portion 26 of the dilator body 24 extends beyond the distal end of the introducer sheath 16.

Figure 2A:
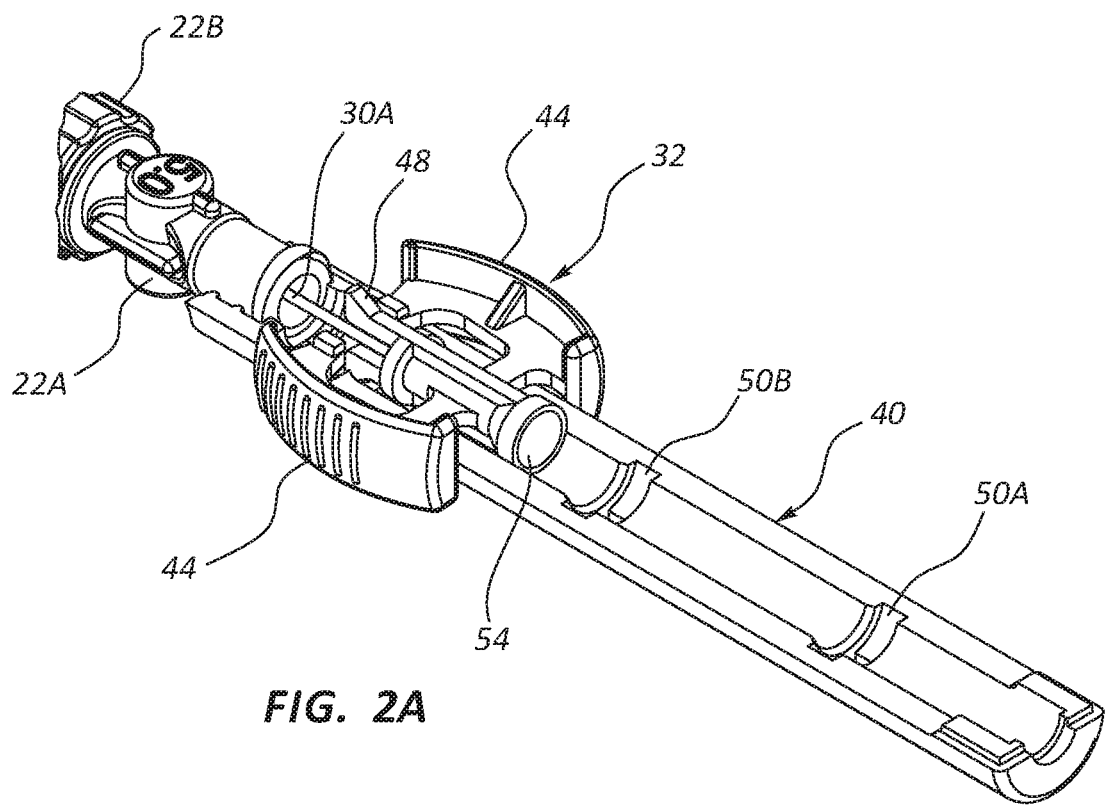
FIGS. 2A and 2B are partial cutaway views of the insertion device of FIGS. 1A-1C.
Figure 2B:
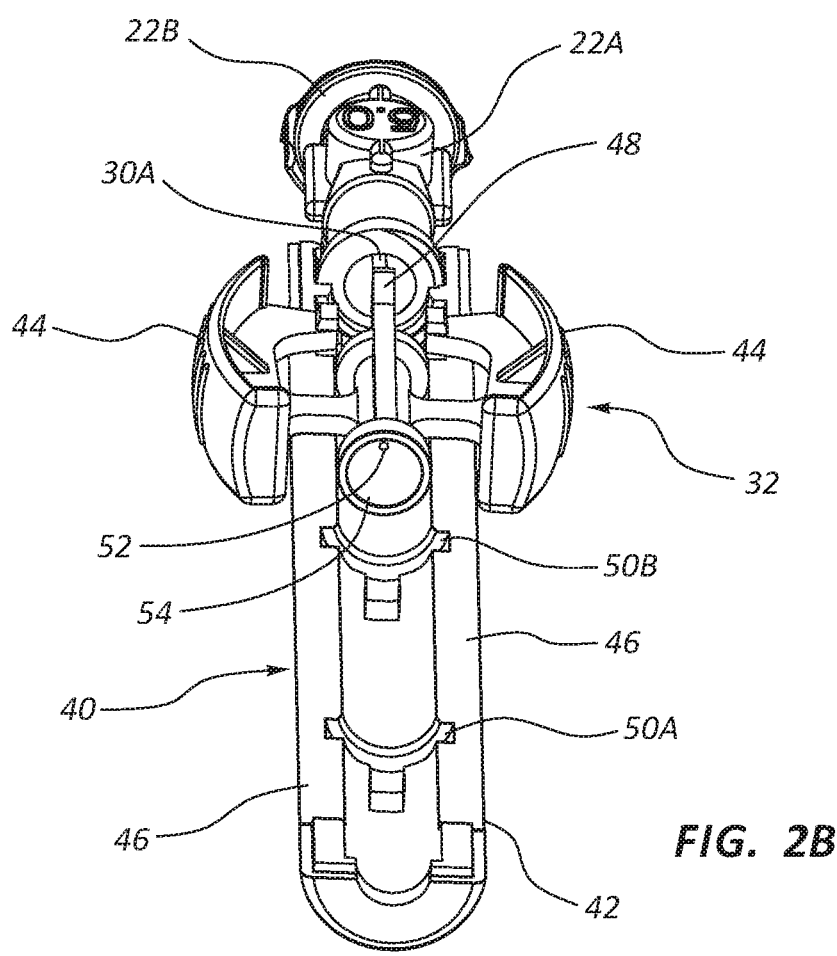

FIGS. 1A-1C further show a hollow needle 30 coaxially disposed within the bore of the dilator 20 such that a sharpened distal tip 30B thereof initially extends distally past the tapered portion 26 of the dilator 20. A proximal end 30A of the needle 30 is connected to a needle hub 32 (FIGS. 2A, 2B). The needle hub 32 cooperates with a needle retraction assembly 40 to selectively move the needle 30 axially with respect the introducer assembly, as will be described. A flash hole 34 can be included in the wall of the needle 30 near the distal tip 30B thereof in order to help detect the presence of blood and confirm positioning of the needle distal tip within a vein, for instance. The flash hole or other suitable component for confirming the presence of blood in the needle in other embodiments may be placed in other locations on the device. In one embodiment, for instance, a flash window can be provided in or near the dilator hub base 22A. Also, though hollow here, in other embodiments the needle may be solid.

A needle retraction assembly 40 is included with the insertion device 10 and includes a housing 42 that threadably engages with the base portion 22A of the dilator hub 22. The housing 42 defines a cavity in which is slidably disposed the hub 32 of the needle 30. The needle 30 extends distally from the needle hub 32 through the bore defined by the hub 22 and body 24 of the dilator 20 to extend beyond the tapered distal portion 26 of the dilator, as shown.

Two handles 44 of the needle hub 32 extend exteriorly to the needle retraction housing 42 via a longitudinally extending slot 46 defined in the housing 42. Thus, sliding movement of the needle hub 32 within the housing 42 toward the proximal end thereof causes corresponding proximal movement of the distal tip 30B of the needle 30. Likewise, distal movement of the needle hub 32 within the housing 42 toward the distal end thereof causes corresponding distal movement of the needle distal tip 30B. It is thus seen that the handles 44 provide one way of selectively moving the needle hub 32 and needle 30. It should be appreciated, however, that other structures or methods may be used to selectively move the needle, including springs or other biasing elements, automatic or machine or electronic-based actuators, etc. Also, though present in the illustrated embodiment, it is appreciated that in other embodiments no housing is included with the needle retraction assembly.

FIGS. 2A and 2B depict further details regarding the needle hub 32 and needle retraction assembly 40. A needle hub position locking feature is included with the needle hub 32, here implemented as two opposing teeth 48 radially extending from the needle hub. The teeth 48 are configured to engage notches 50 included with the housing 42 when the needle hub 32 is axially slid within the housing, thus locking the needle hub at predetermined locations within the needle retraction assembly housing 40. In particular, a proximal notch 50A and a distal notch 50B are included in the housing 42 and will be described further below.

As best seen in FIG. 2B, the needle hub 32 further defines a conduit 52 coaxial with the hollow needle 30 so as to be able to pass a guidewire, such as the guidewire 60 shown in FIG. 3A, through the housing 42, needle hub, and needle of the insertion device 10 such that the guidewire extends past the distal tip 30B of the needle. A conical structure 54 is defined at the proximal end of the conduit 52 to ease insertion of the guidewire 60 into the needle hub 32. In another embodiment, no guidewire is included with the insertion device, and no guidewire conduits are provided.

In accordance with the present embodiment, the needle 30 of the insertion device 10 is axially movable with respect to the introducer assembly. As mentioned above, the needle retraction assembly 40 includes structure to enable the needle to be selectively moved in order to facilitate ease of insertion of a medical device in which the insertion device 10 is disposed, in this case an introducer assembly (FIGS. 1A-1C). Note that though an introducer assembly is shown here, in other embodiments a variety of medical devices can be inserted into a patient with the assistance of the insertion device described herein, as illustrated further below.

In particular, FIG. 3A shows a first position of the needle 30 with respect to the sheath 12 and dilator 20 of the introducer assembly, wherein the distal tip 30B of the needle extends distally beyond the distal end of the dilator body 24 a predetermined distance. This extension of the needle distal tip 30B corresponds to the position of the needle hub 32 proximate the distal end of the housing 42 of the needle retraction assembly 40, as seen in FIGS. 2A and 2B. This position of the distal tip 32B of the needle 30 is also referred to herein as position 1. In position 1, the needle 30 is positioned to gain access to an internal portion of the body of the patient, such as a vein or other vessel. The guidewire 60 is also shown slidably disposed within, and extending through, the needle retraction assembly 40 and the introducer assembly so as to extend distally from the needle distal tip 32B.

Note that the particular distance of needle distal tip extension past the dilator distal end in other embodiments can vary according to various factors, including needle length, distance of needle hub travel within the needle retraction assembly housing, length of the medical device, etc.

FIG. 3B shows a second position of the needle 30 with respect to the sheath 12 and dilator 20 of the introducer assembly, wherein the distal tip 30B of the needle extends distally beyond the distal end of the dilator body 24 a relatively short distance so as to be proximate to the distal end of the tapered distal portion 26 of the dilator body 24. This position of the needle distal tip 30B is achieved when the needle hub 32 is manually slid via user force on the needle hub handles 44 from the position shown in FIG. 3A to the position shown in FIG. 3B, wherein the needle hub is located about mid-way along the length of the needle retraction assembly housing 42. In this position, the teeth 48 of the needle hub 32 frictionally engage the notch 50B, thus locking the needle hub in place until sufficient user force on the handles 44 dislodges it from its location.

The position of the distal tip 32B of the needle 30 in FIG. 3B is also referred to herein as position 2. In position 2, the distal tip 30B of the needle 30 is positioned to assist the tapered distal portion 26 of the dilator body 24 in gaining access to the vessel or other internal body portion of the patient, as will be seen.

FIG. 3C shows a third position of the needle 30 with respect to the sheath 12 and dilator 20 of the introducer assembly, wherein the distal tip 30B of the needle is retracted within the bore of the dilator body 24 so as to be shielded from contact by the dilator body and the body 16 of the introducer 12. This position of the needle distal tip 30B is achieved when the needle hub 32 is manually slid via user force on the needle hub handles 44 from the substantially mid-line position shown in FIG. 3B to the position shown in FIG. 3C, wherein the needle hub is located about proximate the proximal end of the needle retraction assembly housing 42. In this position, the teeth 48 of the needle hub 32 frictionally engage the proximal notch 50A, thus locking the needle hub in place until sufficient user force on the handles 44 dislodges it from its location.

The position of the distal tip 32B of the needle 30 in FIG. 3C is also referred to herein as position 3. In position 3, the distal tip 30B of the needle 30 is retracted and is disposed proximal to the tapered distal portion 26 of the dilator body 24 so as to enable the distal portion of the introducer assembly to flex during advancement into the vessel of the patient, as will be seen. Also, with the needle distal tip 30B safely disposed within the dilator body 24, position 3 prevents the risk of damage to the vessel by the needle 30 while the dilator 20 and introducer 12 are advanced into the vessel. Note further that, though it is described herein as movement of the needle relative to the stationary introducer/dilator, in other embodiments, the introducer and/or dilator can be moved relative to the stationary needle to achieve the three positions described above.

In addition to the teeth and notch locking arrangement described above, it is appreciated that other features for locking the needle hub position with respect to the housing of the needle retraction assembly can be employed as appreciated by one skilled in the art. Also, the number and needle distal tip locations possible with the insertion device can vary from what is described herein. Moreover, the size, shape, and configuration of the insertion device and the medical device it is configured to insert into the body can vary from what is shown and described herein.

Figure 4A:
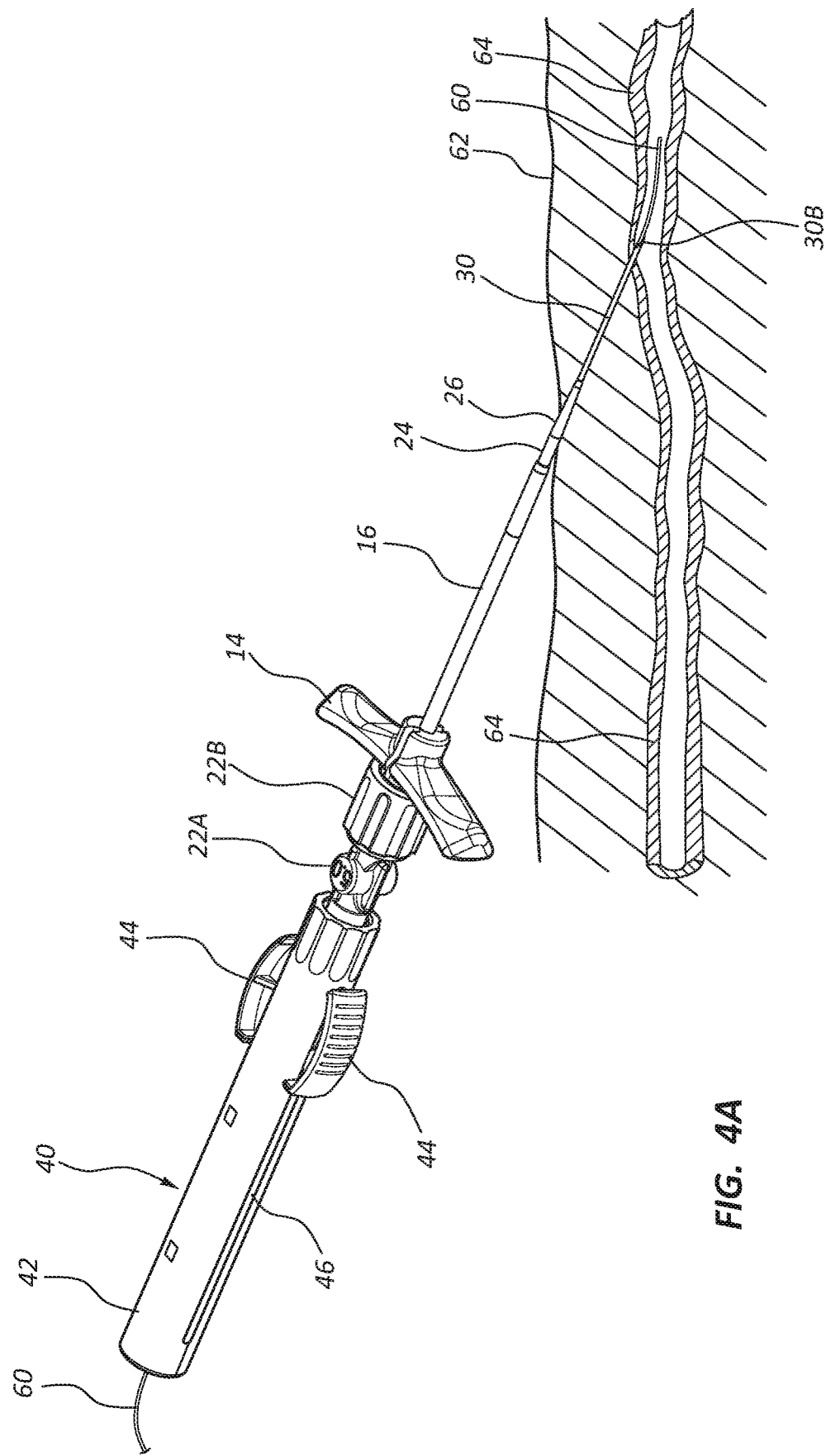
FIGS. 4A-4E show various stages of insertion of an introducer into a patient using an insertion device, according to one embodiment.

FIGS. 4A-4E depict various details regarding the use of the insertion device 10 in assisting with the insertion of an introducer assembly into a vessel of a patient, according to one embodiment. Note that the medical device to be placed and the desired location within the patient body where the device is to be placed can vary from what is described here. In FIG. 4A, the insertion device 10, having been previously attached to the introducer assembly as explained above and with the needle 30 in position 1 (FIG. 3A), the distal tip 30B of the needle is inserted into the skin 62 of the patient and into the lumen of a desired subcutaneous vessel 64. A flash hole 34 (FIG. 1A) defined in the needle 30 can assist in viewing blood return up the needle so as to confirm proper needle placement in the vessel 64, in one embodiment. Once the vessel 64 has been accessed, the guidewire 60 can be manually advanced by the user through the housing 42 of the needle retraction assembly and the needle 30 so as to extend into the vessel lumen.

Figure 4B:
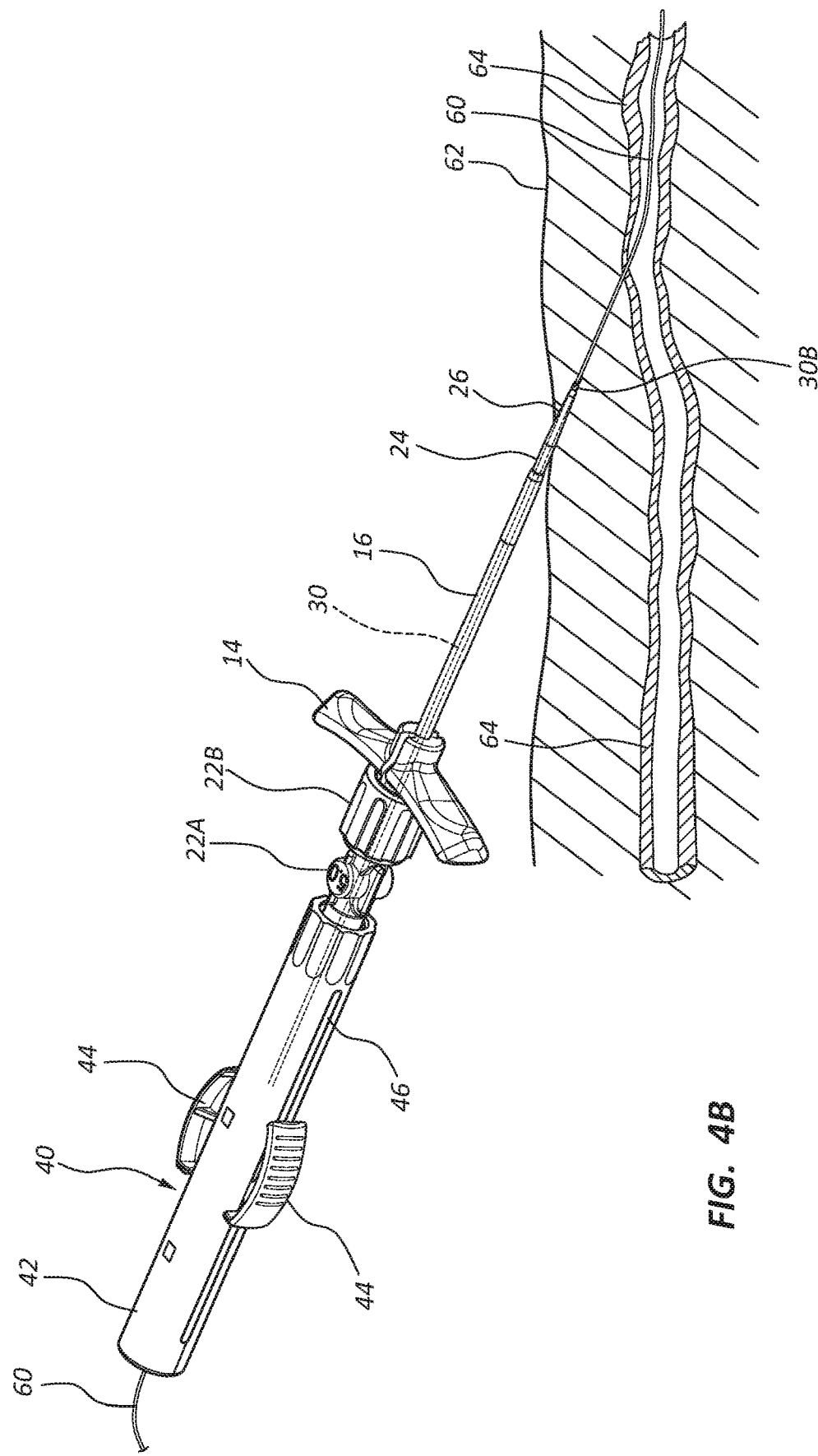
Figure 4C:
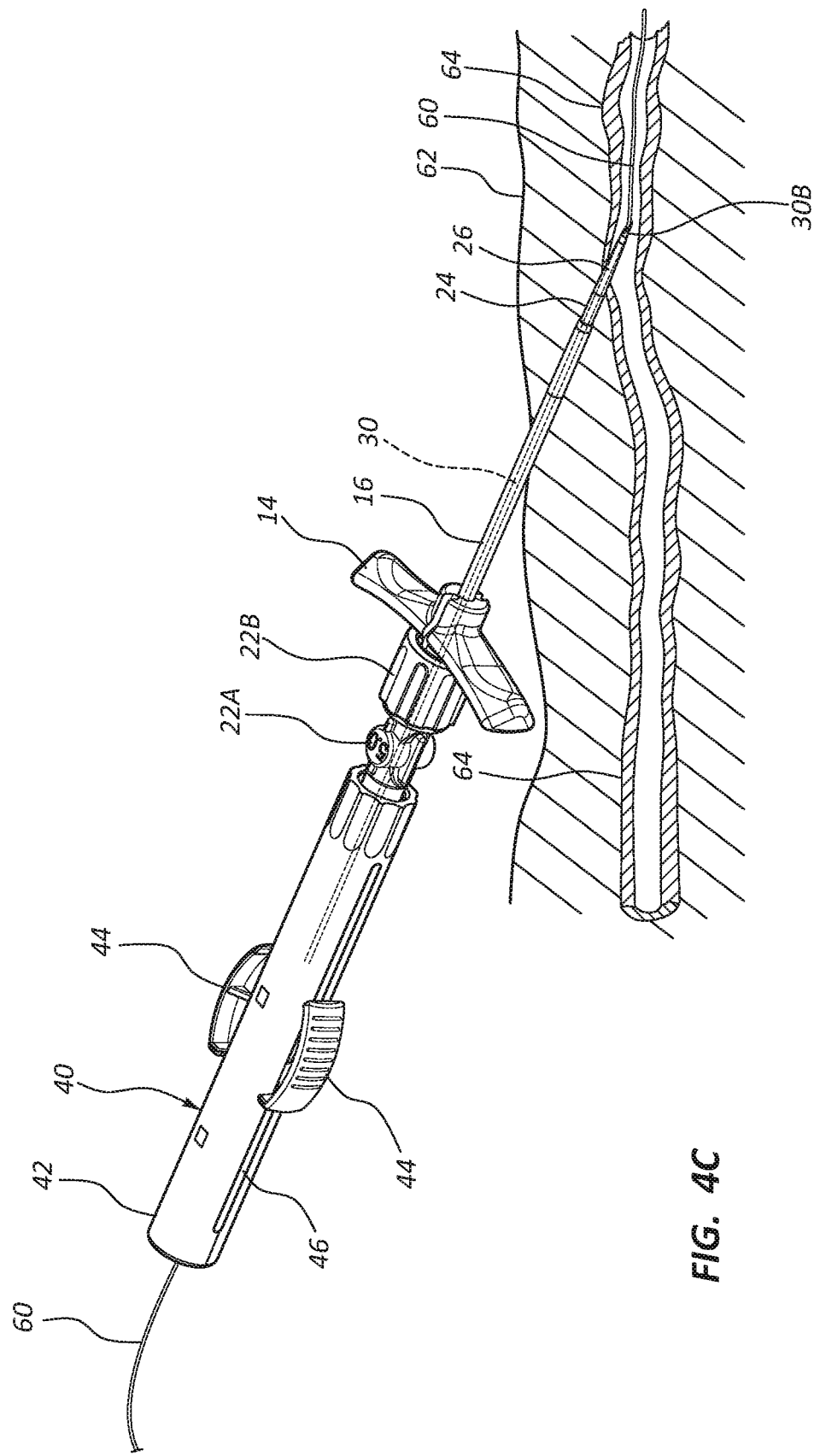

In FIG. 4B, once the guidewire has been inserted into the vessel 64, the needle 30 is retracted to position 2 (FIG. 3B) such that the needle distal tip 30B is proximate the tapered distal portion 26 of the dilator body 24. This may cause the needle distal tip to retract a short distance from the vessel insertion site, as shown, while the guidewire 60 remains in place within the vessel 64 and extending through the vessel insertion site.

Retraction of the needle 30 to position 2 enables the distal tip 30B thereof to assist entry of the tapered distal portion 26 of the dilator body 24 through the vessel insertion site and into the vessel 64 by following the previously placed guidewire 60. It is noted that in one embodiment the needle or another suitable portion of the insertion device or medical component can be treated so as to be ultrasonically visible such that one or more of the stages described herein can be performed with the assistance of ultrasound imaging guidance.

Figure 4D:
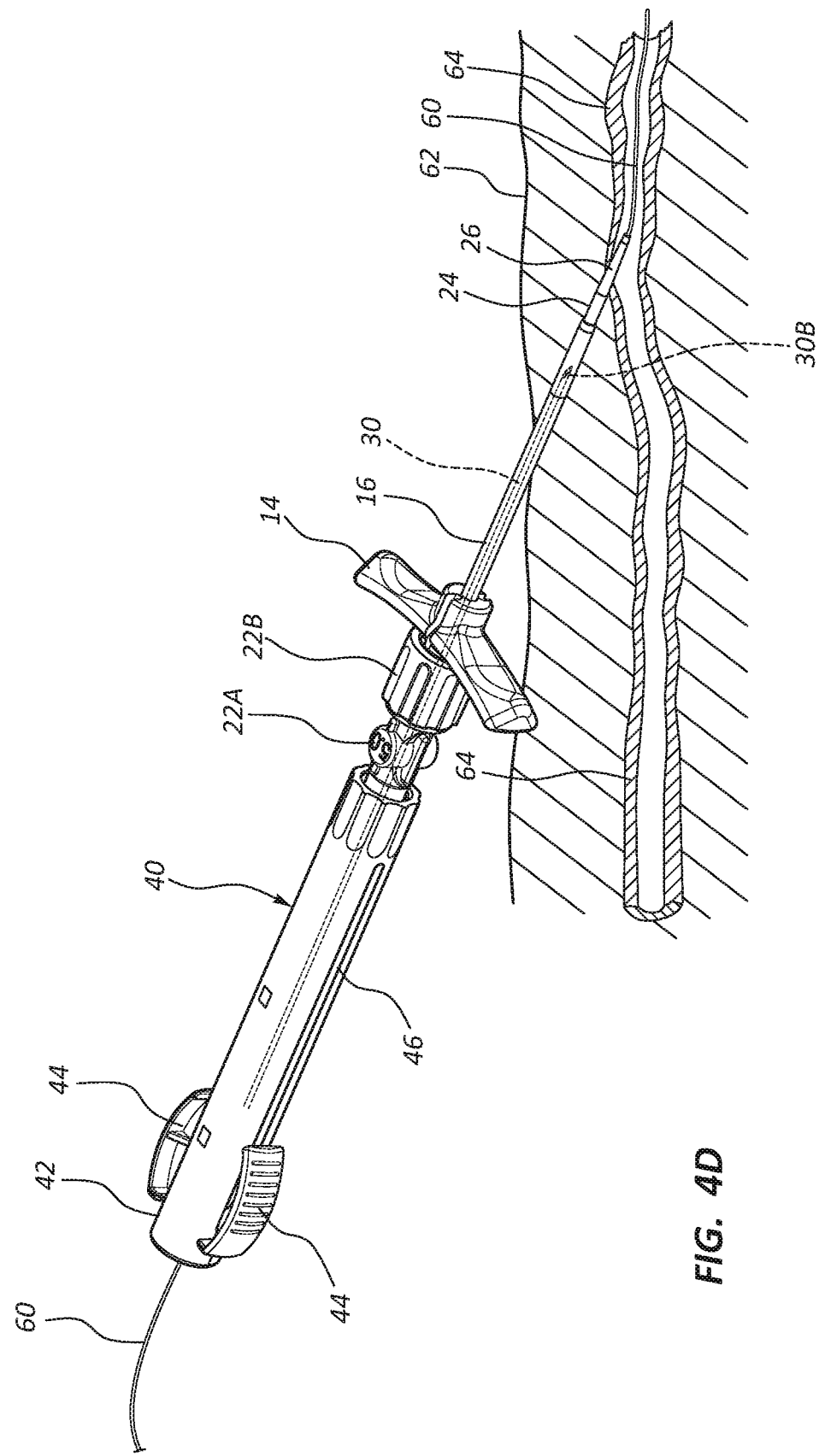

FIG. 4D shows that, once the needle distal tip 30B and tapered distal portion 26 of the dilator body 24 are disposed within the vessel 64, the needle can be retracted to position 3 (FIG. 3C), wherein the distal tip thereof is disposed within the bore of the dilator body 24 a predetermined proximal to the dilator distal end. As has been described, and as is the case with the other needle positions, the needle retraction assembly 40 releasably locks the needle hub 32 in position so the needle distal tip can remain shielded within the dilator bore in position 3. With the needle 30 in position 3, the dilator 20 and introducer 12 can be further advanced distally into the vessel 64 until inserted to the desired extent within the vessel. Because the needle 30 is not present in their distal portions, the introducer 12 and dilator 20 are pliant so as to bend and conform to the shape of the vessel 64.

Figure 4E:
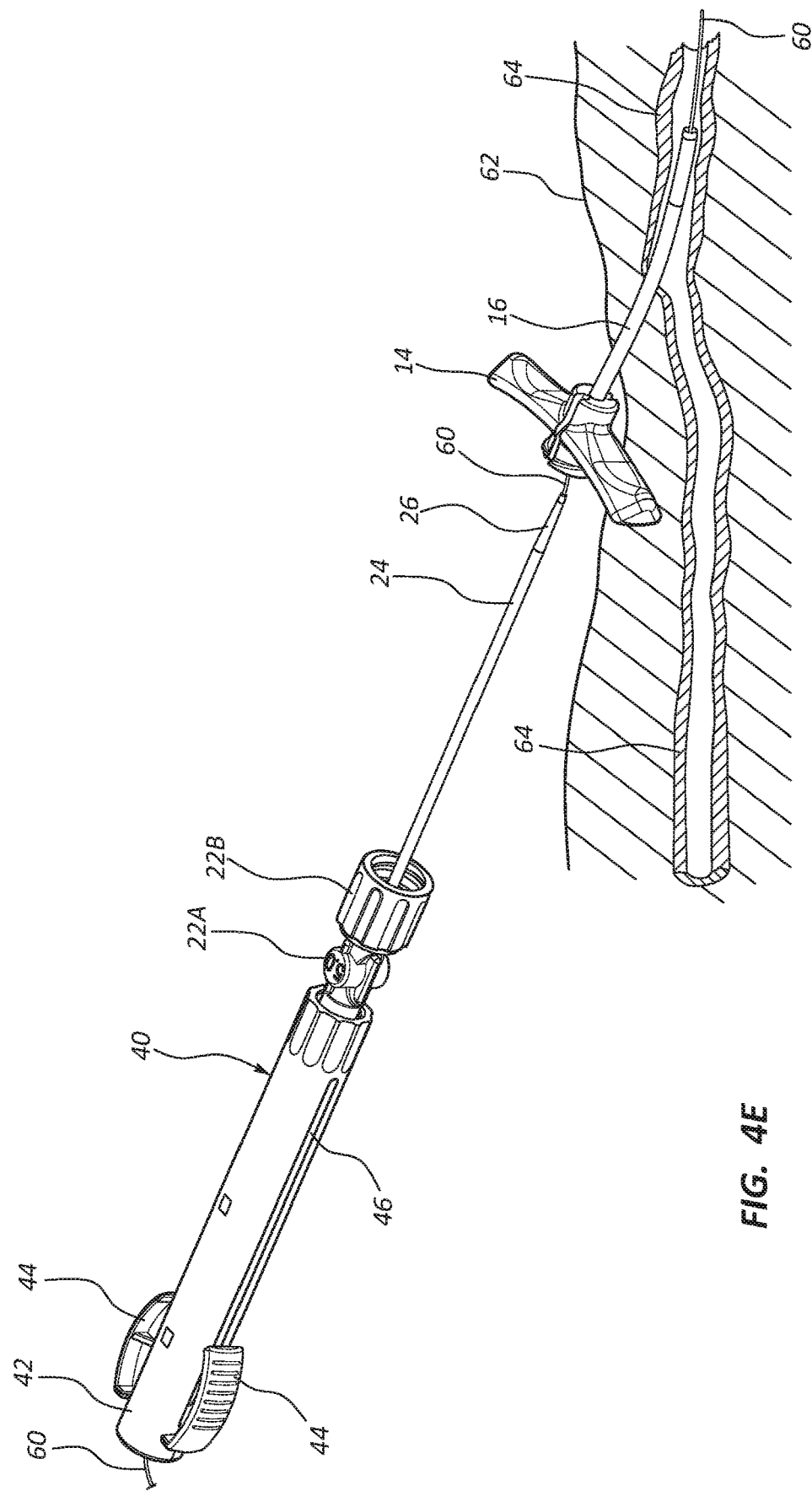

FIG. 4E shows that once the introducer 12 has been inserted a sufficient distance into the vessel 64, the insertion device 10 including the needle 30 and the needle retraction assembly 40, together with the dilator 20, can be removed, thus separating them from the introducer and leaving the introducer disposed within the vessel. A catheter may then be inserted into the vessel 64 through the introducer 12.

If desired, the guidewire 60 can be left in place within the vessel 64 when the insertion device 10 and dilator 20 are removed, as seen in FIG. 4E, to further assist in placement of a catheter or other suitable device through the introducer 12. It is further appreciated that the above method may be performed without the use of a guidewire, in one embodiment.

It is appreciated that catheters of many types, including PICC, PIV, intermediate dwell or mid-line, CVC, and other catheter configurations, can be placed with the present insertion device. Other uses of the insertion device are also contemplated. Non-limiting examples of such other uses include placement of stent grafts, feeding devices, etc. The insertion device is suitable for arterial or venous vessel access, and for use in various body cavities or intracorporeal locations. As mentioned, in the present embodiment the needle 30 is positionable in three positions; however, other possible needle position configurations are also contemplated.

Figure 5A:
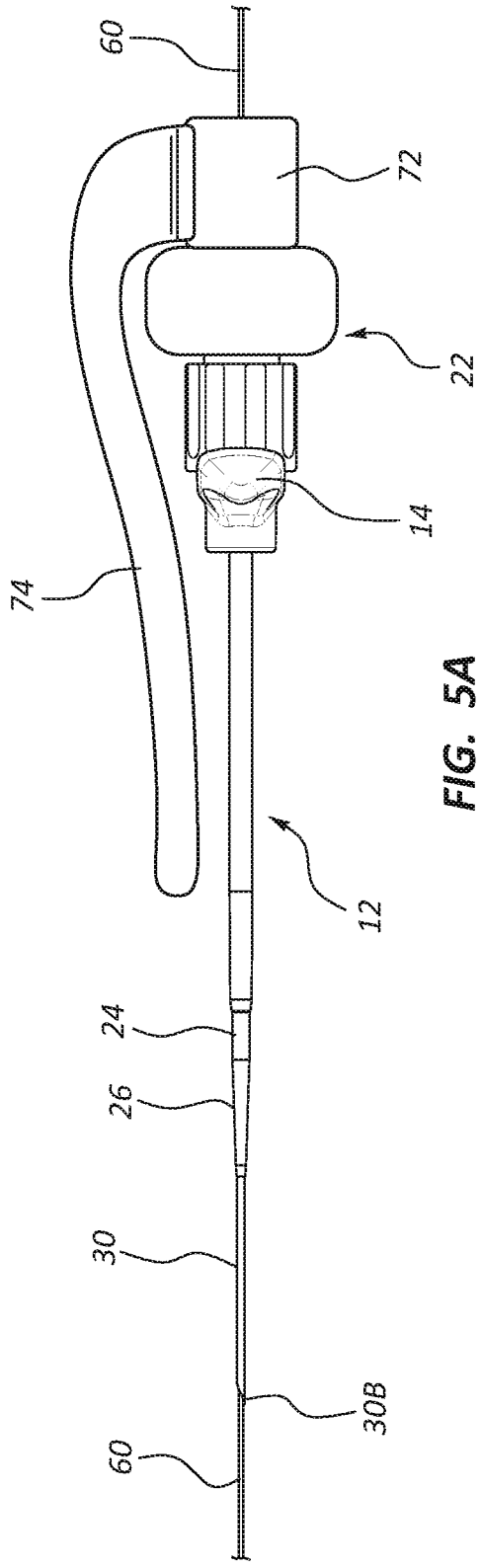
FIGS. 5A and 5B show an insertion device according to one embodiment.
Figure 5B:
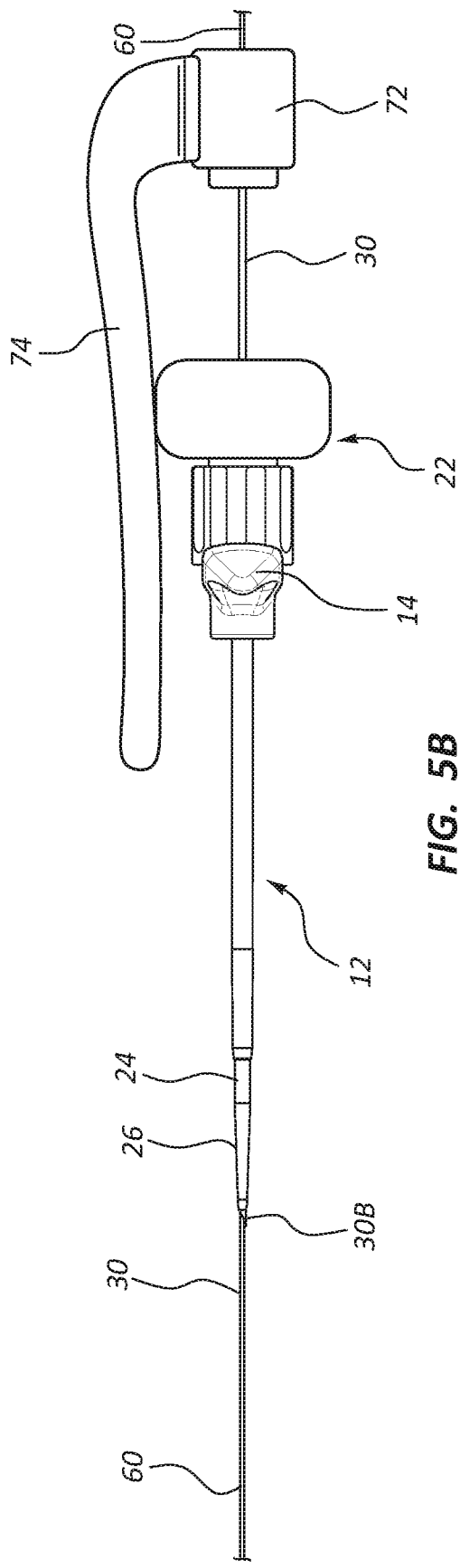

FIGS. 5A and 5B depict the insertion device according to another embodiment, wherein the needle retraction assembly includes no housing. Rather, the needle hub 72 includes a distally extending handle that is shaped and positioned to facilitate one-handed operation of the device, such as retraction of the needle 30, shown in FIG. 5B. These and other variations of the insertion device are therefore contemplated.

Figure 6:
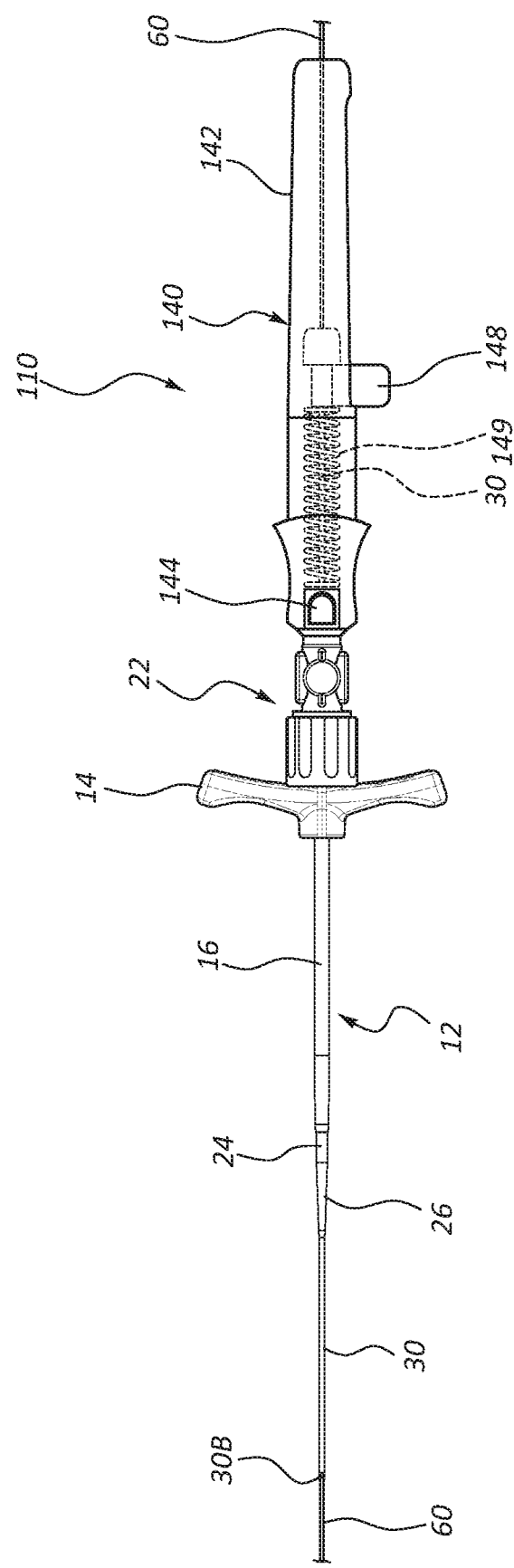
FIG. 6 is a top view of an insertion device according to one embodiment.

FIG. 6 shows details of an insertion device 110 according to one embodiment, wherein a needle retraction assembly 140 includes a housing 142 through at least a portion of which the guidewire 60 extends. A button release 144 is included on the housing 142 for selectively retracting the needle 30 from its position 1, illustrated here, to another position, such as position 2 or position 3 described above. In one embodiment, the button release 144 is operably coupled to a spring 149 or other biasing element disposed within the housing 142 in order to cause retraction of the needle 30. The housing 142 of the needle retraction assembly 140 further includes a handle 148 for selectively advancing the guidewire 60 through the needle 30. Though illustrated in FIG. 6 as extending past the proximal end of the insertion device, the guidewire in another embodiment can be completely contained within the housing of the needle retraction assembly.

Figure 7A:
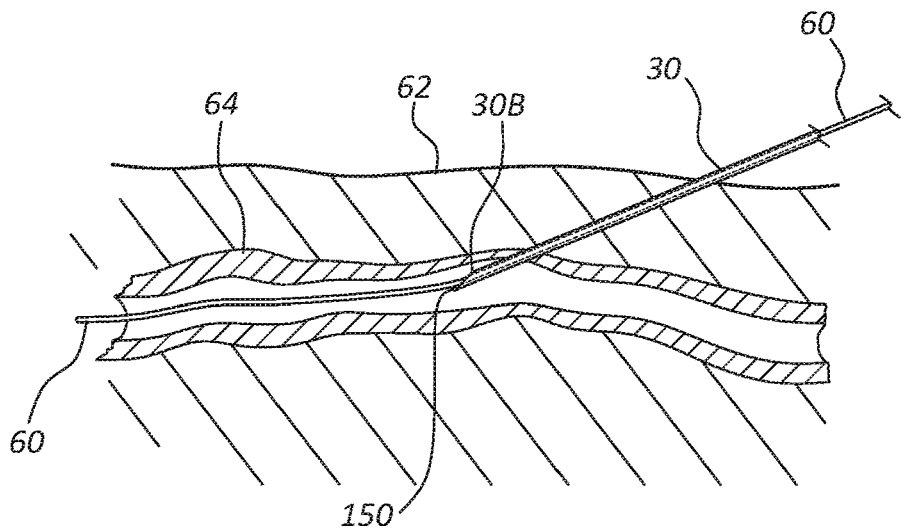
FIGS. 7A-7C show details of insertion of the needle of the insertion device of FIGS. 1A-1C according to one embodiment.
Figure 7B:
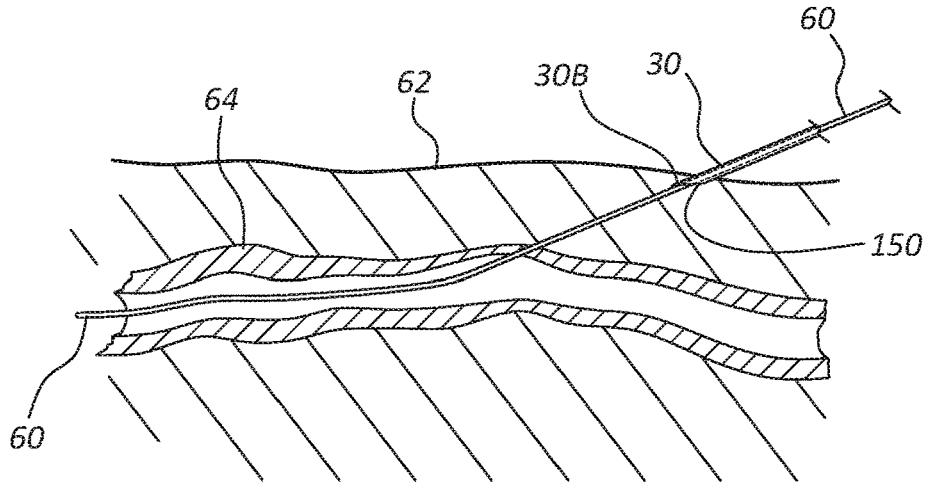
Figure 7C:
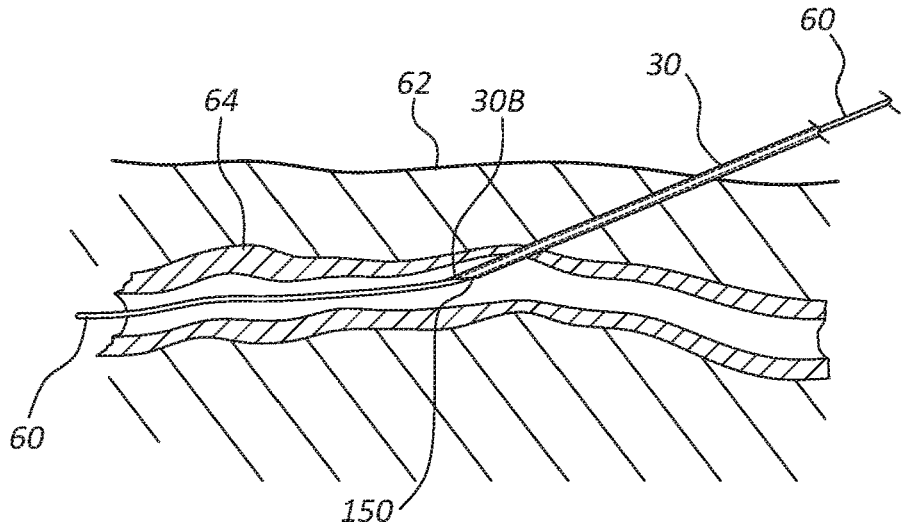

FIGS. 7A-7C illustrate that, in one embodiment, it is desirable to rotate a bevel 150 of the needle 30 from a bevel-up configuration to a bevel-down configuration when moving the needle from position 1 (FIG. 3A) to position 2 (FIG. 3B). In particular, FIG. 7A shows insertion of the needle 30 into the vessel 64 while in position 1, with the bevel 150 of the needle distal tip 30B in an up position, i.e., the angled cutting surface of the needle facing toward the surface of the skin 62. FIG. 7B shows that when the needle 30 is retracted to position 2, the bevel 150 can be rotated to a bevel-down configuration. FIG. 7C shows that the needle 30 can then be reinserted into the vessel 64 while in the bevel-down configuration, as was described in connection with FIGS. 4B and 4C above. This desirably helps to prevent gouging of the vessel 64 caused by inadvertent needle contact with the back wall of the vessel during needle insertion and advancement. In addition, the bevel-down configuration reduces the chance of guidewire severing by the needle distal tip 30B when the needle 30 is advanced into the vessel 64 over the guidewire 60.

Figure 8:
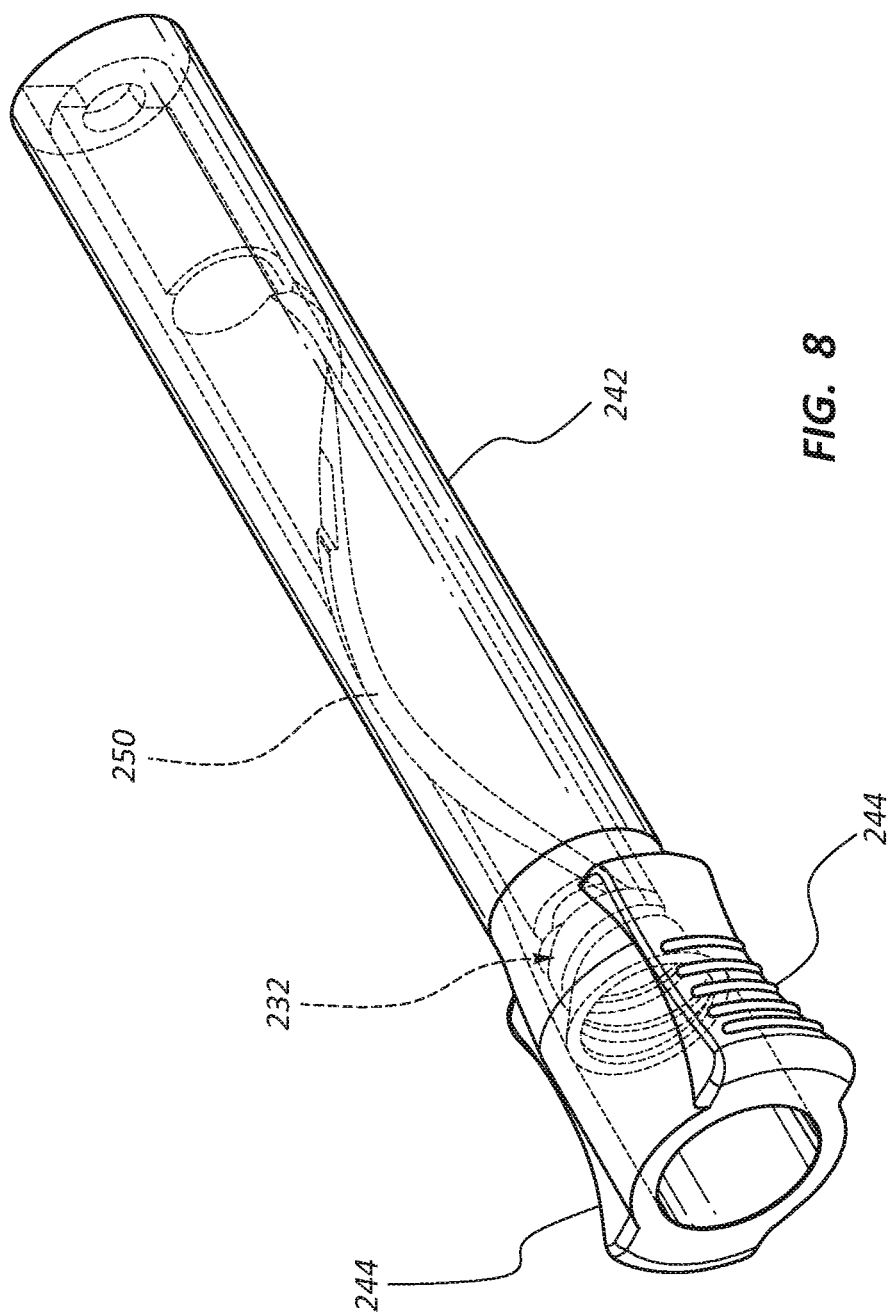
FIG. 8 shows a housing of an insertion device according to one embodiment.

FIG. 8 shows one example of a structure for facilitating rotation of the bevel 150 of the needle distal tip 30B described above, wherein a housing 242 of the needle retraction assembly includes a needle hub 232 that is slidably disposed therein. Handles 244 of the needle hub 232 extend through the wall of the housing 242 to enable manual translation of the needle hub along the length of the housing. The internal portion the needle hub 232 is operably connected to a spiral track 250 defined by the inner wall of the housing 242, which enables the needle hub to rotate about its sliding axis as it is moved proximally within the housing. As a proximal end of the needle 30 is fixedly secured to the needle hub 32, rotation of the needle hub desirably causes corresponding rotation of the needle distal tip bevel 150, as seen in FIGS. 7A-7C. In addition to this, other structures for causing needle tip bevel rotation can also be employed in the insertion device.

Figure 9A:
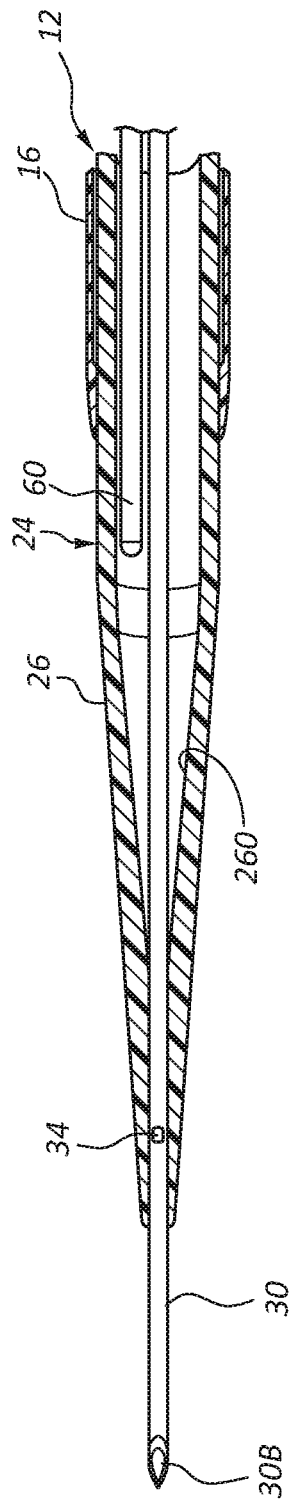
FIGS. 9A-9C show a distal portion of an insertion device according to one possible embodiment.
Figure 9B:
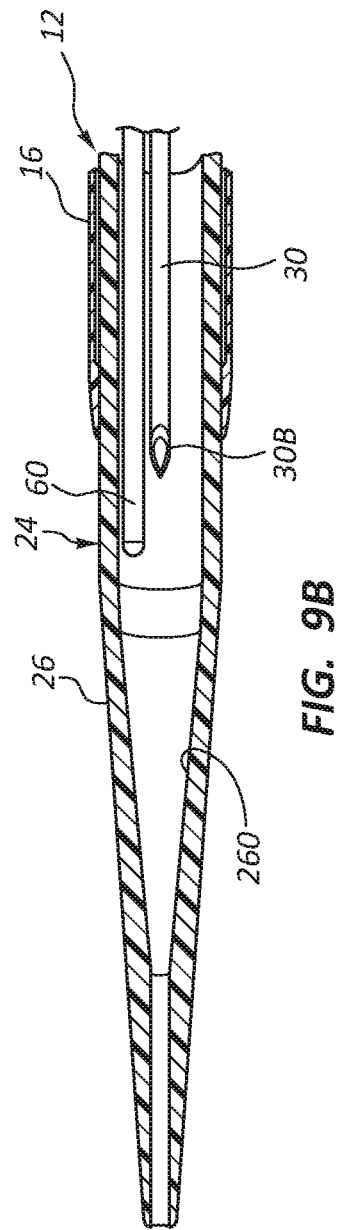
Figure 9C:
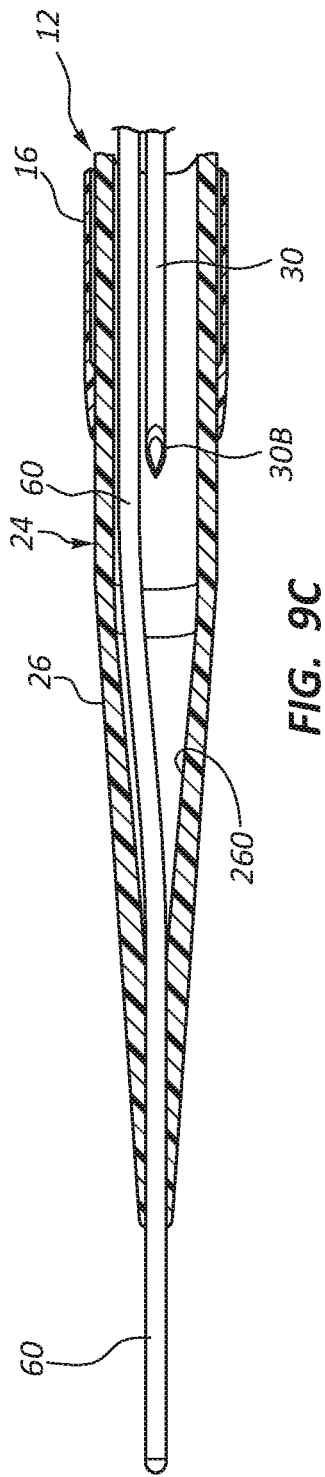

FIGS. 9A-9C show details of a distal portion of the insertion device according to one embodiment, wherein the guidewire 60 is not disposed within the hollow needle 30, but rather is disposed alongside the needle within the bore 260 of the dilator 20. Particularly, in FIG. 9A the needle 30 is shown extended in position 1, with the guidewire retracted within the dilator bore 260. In FIG. 9B, the needle is retracted into the dilator bore 260 in position 3. In FIG. 9C, the guidewire 60 is extended past the distal end of the dilator bore 260. The needle and guidewire configuration shown in FIGS. 9A-9C is useful for implementations where a guidewire that is larger than what would otherwise fit within the needle is desired to be used, or in cases where a relatively smaller needle is desired to be used so as to reduce patient discomfort and excess bleeding.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A medical insertion device, comprising:
   an introducer assembly, including a dilator coaxially disposed in a sheath, the dilator removably engaged to the sheath in an insertion configuration;
   a needle coaxially disposed in the dilator, the needle having a distal tip and a proximal end coupled to a needle hub; and
   a housing removably engaged to the dilator, the needle hub movably disposed in the housing between a first locked position, a second locked position, and a third locked position, wherein:
      the distal tip of the needle extends a first length from a distal end of the dilator in the first locked position;
      the distal tip of the needle extends a second length from the distal end of the dilator in the second locked position, the second length less than the first length; and
      the distal tip of the needle is within the dilator in the third locked position.

2. The medical insertion device according to claim 1, wherein the dilator includes a dilator hub and the sheath includes a sheath hub, the dilator hub threadably engaged to the sheath hub in the insertion configuration.

3. The medical insertion device according to claim 2, wherein the dilator hub is threadably engaged to the sheath hub in the first, second, and third locked positions.

4. The medical insertion device according to claim 2, wherein the housing is threadably engaged to the dilator hub.

5. The medical insertion device according to claim 1, further comprising a handle coupled to the needle hub through a wall of the housing.

6. The medical insertion device according to claim 5, wherein the housing includes a track, the needle hub coupled to the track such that movement of the handle with respect to the housing correspondingly moves the needle hub along the track.

7. The medical insertion device according to claim 6, wherein the track is curved such that movement of the needle hub from the first locked position to the second locked position rotates the needle tip from a first orientation to a second orientation different from the first orientation.

8. The medical insertion device according to claim 6, wherein the track defines a spiral path.

9. The medical insertion device according to claim 1, wherein the needle hub includes at least one protrusion and the housing includes at least one recess for receiving the at least one protrusion at each of the first, second, and third locked positions.

10. The medical insertion device according to claim 1, wherein the dilator includes a tapered distal portion, the distal tip of the needle in the second locked position providing a transition for the tapered distal portion.

11. The medical insertion device according to claim 1, wherein the needle hub includes a distally extending handle to enable one-handed grasping of the insertion device and movement of the needle hub between the first, second, and third locked positions.

12. The medical insertion device according to claim 1, further comprising a biasing element coupled to the needle hub, and a guidewire coupled to a guidewire handle.

* * * * *